(12) United States Patent
Fukuda

(10) Patent No.: US 10,827,914 B2
(45) Date of Patent: Nov. 10, 2020

(54) ENDOSCOPE SYSTEM AND CHARACTERISTIC AMOUNT CALCULATION METHOD

(71) Applicant: HOYA CORPORATION, Tokyo (JP)

(72) Inventor: Masaaki Fukuda, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 91 days.

(21) Appl. No.: 16/318,294

(22) PCT Filed: Sep. 1, 2017

(86) PCT No.: PCT/JP2017/031675
§ 371 (c)(1),
(2) Date: Jan. 16, 2019

(87) PCT Pub. No.: WO2018/043728
PCT Pub. Date: Mar. 8, 2018

(65) Prior Publication Data
US 2019/0239735 A1    Aug. 8, 2019

(30) Foreign Application Priority Data

Sep. 2, 2016    (JP) .................................. 2016-171955

(51) Int. Cl.
*A61B 1/06*    (2006.01)
*A61B 1/00*    (2006.01)
(Continued)

(52) U.S. Cl.
CPC ........ *A61B 1/0638* (2013.01); *A61B 1/00009* (2013.01); *A61B 1/045* (2013.01);
(Continued)

(58) Field of Classification Search
CPC . A61B 1/00009; A61B 1/0638; A61B 1/0646; A61B 1/0676
See application file for complete search history.

(56) References Cited

U.S. PATENT DOCUMENTS

2002/0177780 A1* 11/2002 Sendai .................. A61B 1/045
                                                      600/476
2012/0215066 A1*  8/2012 Akiyama ................ A61B 1/05
                                                      600/109
(Continued)

FOREIGN PATENT DOCUMENTS

| CN | 105324064 A | 2/2016 |
| JP | 5302984 B | 10/2013 |

(Continued)

OTHER PUBLICATIONS

PCT/JP2017/031675 International Search Report, dated Nov. 14, 2017.

(Continued)

*Primary Examiner* — David Bilodeau
(74) *Attorney, Agent, or Firm* — Kilpatrick Townsend & Stockton LLP

(57) ABSTRACT

An endoscope system generates first to third color image data by imaging biological tissue illuminated with first to third light. The endoscope system uses a first light intensity ratio of the first light and the second light, and/or an imaging sensitivity of the image sensor, to correct a first ratio between multiple components of the first and second color image data, and the endoscope system calculates a first characteristic amount of the biological tissue based on the first corrected ratio. Furthermore, the endoscope system uses a second light intensity ratio between the second light and the third light to correct a second ratio between multiple components of the second and third color image data, and the endoscope system calculates a second characteristic amount of the biological tissue based on the second corrected ratio and the first characteristic amount.

17 Claims, 6 Drawing Sheets

(51) Int. Cl.
*A61B 1/045* (2006.01)
*G02B 23/24* (2006.01)
*G02B 23/26* (2006.01)

(52) U.S. Cl.
CPC .......... *A61B 1/0676* (2013.01); *A61B 1/0646* (2013.01); *G02B 23/2461* (2013.01); *G02B 23/26* (2013.01)

(56) References Cited

U.S. PATENT DOCUMENTS

| 2014/0184769 | A1* | 7/2014 | Ishihara | G06T 5/50 |
| | | | | 348/68 |
| 2015/0091447 | A1* | 4/2015 | Kubo | A61B 1/045 |
| | | | | 315/153 |
| 2016/0120449 | A1 | 5/2016 | Chiba | |
| 2016/0146723 | A1 | 5/2016 | Chiba | |

FOREIGN PATENT DOCUMENTS

| JP | 2016-97067 A | 5/2016 |
| WO | 2014192781 A1 | 12/2014 |

OTHER PUBLICATIONS

CN201780037566.3, "Office Action" with Machine translation, dated Sep. 28, 2020, 14 pages.

\* cited by examiner

ENDOSCOPE SYSTEM AND CHARACTERISTIC AMOUNT CALCULATION METHOD

CROSS-REFERENCE TO RELATED APPLICATIONS

This application is a 371 U.S. National Phase of PCT International Application No. PCT/JP2017/031675 filed on Sep. 1, 2017, which claims benefit and priority to Japanese patent application No. 2016-171955 filed on Sep. 2, 2016, and which is incorporated by reference herein in its entirety.

TECHNICAL FIELD

The present disclosure relates to an endoscope system that acquires biological information (characteristic amounts) of biological tissue based on image data generated by imaging the biological tissue, and a characteristic amount calculation method for obtaining biological information (characteristic amounts) of biological tissue from image data.

BACKGROUND ART

An endoscope system has been known which includes a function of obtaining information on a biological substance in biological tissue, which is an imaging subject, such as information on an amount of hemoglobin and an oxygen saturation of hemoglobin, based on image data obtained by an endoscope. An example of this kind of endoscope system is disclosed in Patent Document 1.

With the endoscope system disclosed in Patent Document 1, a blood amount (amount of hemoglobin) is calculated based on a ratio R2/G2 between a red-color signal R2 in a wavelength range of 590 to 700 nm and a green-color signal G2 in a wavelength range of 540 to 580 nm among pixel signals of a captured image of biological tissue illuminated with white light, and furthermore, an oxygen saturation of the hemoglobin is calculated based on a ratio B1/G2 between a blue-color signal B1 among pixel signals of a captured image of biological tissue illuminated with oxygen concentration measurement light (narrow-band light of 473 nm) and the green-color signal G2 among the pixel signals of the captured image of the biological tissue illuminated with the white light. Accordingly, information on the oxygen saturation of the hemoglobin can be displayed.

CITATION LIST

Patent Documents

Patent Document 1: JP 5302984A

SUMMARY OF DISCLOSURE

Technical Problem

In the above-described endoscope system, since the ratio B1/G2 is calculated using the oxygen saturation measurement light and the white light, if the light intensity of the oxygen saturation measurement light and the white light differ depending on the apparatus (if there is variation depending on the apparatus), the ratio B1/G2 also varies depending on the apparatus. The variation of the light intensity cannot be completely eliminated. For this reason, there is a risk that the oxygen saturation of the hemoglobin calculated based on the ratio B1/G2 will also vary between apparatuses. For this reason, the oxygen saturation cannot be obtained accurately. In particular, a malignant tumor or the like is determined using the fact that the oxygen saturation is low, and therefore it is more difficult to perform suitable determination.

The present disclosure has been made in view of the foregoing circumstance, and it is an object thereof to provide an endoscope system and a characteristic amount calculation method according to which it is possible to obtain highly-accurate information on a characteristic amount when obtaining a characteristic amount such as an oxygen saturation of hemoglobin in biological tissue based on image data of the biological tissue illuminated using multiple types of light.

Solution to the Problem

The endoscope system of the present disclosure includes the following aspects.

Aspect 1

An endoscope system, including:

a light source apparatus configured to emit at least first light and second light with different wavelength bands;

an endoscope including an imaging unit that includes an image sensor configured to generate first color image data by imaging biological tissue illuminated with the first light, and to generate second color image data by imaging the biological tissue illuminated with the second light; and a processor including: a storage unit storing a first light intensity ratio, which is a ratio between a light intensity of the first light and a light intensity of the second light; and a characteristic amount acquisition unit configured to acquire a first characteristic amount of the biological tissue based on a first corrected ratio obtained by using the first light intensity ratio to correct a first ratio that is sensitive to the first characteristic amount of the biological tissue, among ratios between a plurality of components of the first color image data of the biological tissue and a plurality of components of the second color image data.

For example, according to a later-described embodiment, the amount of hemoglobin or the oxygen saturation of hemoglobin corresponds to the first characteristic amount. If the amount of hemoglobin corresponds to the first characteristic amount, the white light WL and the wide light of the later-described embodiment correspond to the first light and the second light. Also, if the oxygen saturation of the hemoglobin corresponds to the first characteristic amount, the wide light and the narrow light of the later-described embodiment correspond to the first light and the second light.

Aspect 2

The endoscope system according to Aspect 1, wherein the first light intensity ratio is a ratio between components of color image data of a reference subject, the color image data being generated by imaging the reference subject illuminated with the first light and the second light using the image sensor or a reference image sensor.

For example, the first light intensity ratio G1 or the second light intensity ratio G2 of the later-described embodiment corresponds to the first light intensity ratio.

Aspect 3

The endoscope system according to Aspect 1 or 2, wherein the first light intensity ratio is a ratio for setting a ratio between a value of a luminance component of the first color image data and a value of a luminance component of the second color image data of the reference subject to a certain value.

Aspect 4

An endoscope system, including:

a light source apparatus configured to emit light including at least two light components with different wavelength bands;

an endoscope including an imaging unit that includes an image sensor configured to generate color image data by imaging biological tissue illuminated with the light; and a processor including: a storage unit storing a sensitivity ratio, which is a ratio between imaging sensitivities in different wavelength bands of the light components of the image sensor; and a characteristic amount acquisition unit configured to acquire a first characteristic amount of the biological tissue based on a first corrected ratio obtained by using the sensitivity ratio to correct a first ratio that is sensitive to the first characteristic amount of the biological tissue, among ratios of corresponding components corresponding to wavelength bands of the light components of the color image data of the biological tissue.

Aspect 5

An endoscope system, including;

a light source apparatus configured to emit at least first light and second light with different wavelength bands;

an endoscope including an image capturing unit that includes an image sensor configured to generate first color image data by imaging biological tissue illuminated with the first light, and to generate second color image data by imaging the biological tissue illuminated with the second light; and a processor including; a storage unit storing a sensitivity ratio, which is a ratio between an imaging sensitivity for the first light and an imaging sensitivity for the second light of the image sensor; and a characteristic amount acquisition unit configured to acquire a first characteristic amount of the biological tissue based on a first corrected ratio obtained by using the sensitivity ratio to correct a first ratio that is sensitive to the first characteristic amount of the biological tissue, among ratios between a plurality of components of the first color image data of the biological tissue and a plurality of components of the second color image data of the biological tissue.

For example, according to the later-described embodiment, the sensitivity ratio G2 corresponds to the sensitivity ratio. Also, for example, according to the later-described embodiment, the amount of hemoglobin corresponds to the first characteristic amount and the white light WL and the wide light of the later-described embodiment correspond to the first light and the second light.

Aspect 6

The endoscope system according to Aspect 5, wherein the storage unit stores a first light intensity ratio between a light intensity of the first light and a light intensity of the second light, and the sensitivity ratio is a ratio obtained by using the first light intensity ratio to correct a ratio between components of color image data of a reference subject, the color image data being generated by imaging the reference subject illuminated with the first light and the second light, using the image sensor.

Aspect 7

The endoscope system according to Aspect 6, wherein the characteristic amount acquisition unit acquires the first corrected ratio by correcting the first ratio using the sensitivity ratio and the first light intensity ratio.

Aspect 8

The endoscope system according to any one of Aspects 4 to 7, wherein the sensitivity ratio is a ratio set such that the value of the first corrected ratio obtained when a reference subject for which the value of the first ratio is a known reference value is imaged using the image sensor is the reference value of the reference subject.

Aspect 9

An endoscope system, including:

a light source apparatus configured to emit first light, second light, and third light with different wavelength bands;

an endoscope including an image capturing unit that includes an image sensor configured to generate second color image data by imaging biological tissue illuminated with the second light, and to generate third color image data by imaging the biological tissue illuminated with the third light; and a processor including: a storage unit storing a second light intensity ratio, which is a ratio between a light intensity of the second light and a light intensity of the third light; and a characteristic amount acquisition unit configured to acquire a second characteristic amount of the biological tissue based on a second corrected ratio obtained by using the second light intensity ratio to correct a second ratio that is sensitive to the second characteristic amount of the biological tissue, among ratios between a plurality of components of the second color image data of the biological tissue and a plurality of components of the third color image data of the biological tissue.

For example, according to the later-described embodiment, the white light WL, the wide light, and the narrow light correspond to the first light, the second light, and the third light. Also, for example, according to a later-described embodiment, the oxygen saturation of the hemoglobin corresponds to the second characteristic amount and the second light intensity ratio G2 corresponds to the second light intensity ratio.

Aspect 10

The endoscope system according to Aspect 9, wherein the second light intensity ratio is a ratio between components of color image data of a reference subject, the color image data being generated by imaging the reference subject illuminated with the second light and the third light using the image sensor or a reference image sensor.

Aspect 11

The endoscope system according to Aspect 9 or 10, wherein the imaging unit is configured to generate first color image data by imaging biological tissue illuminated with the first light, using the image sensor;

the storage unit stores a first light intensity ratio, which is a ratio between a light intensity of the first light and the light intensity of the second light, and the characteristic amount acquisition unit includes a first portion configured to acquire a first characteristic amount of the biological tissue based on a first corrected ratio obtained by using the first light intensity ratio to correct a first ratio that is sensitive to the first characteristic amount of the biological tissue, among ratios of a plurality of components of the first color image data of the biological tissue and a plurality of components of the second color image data of the biological tissue, and a second portion configured to acquire the second characteristic amount of the biological tissue based on the first characteristic amount and the second corrected ratio.

For example, according to a later-described embodiment, the amount of hemoglobin corresponds to the first characteristic amount and the first light intensity ratio G1 corresponds to the first light intensity ratio.

Aspect 12

The endoscope system according to Aspect 9 or 10, wherein the imaging unit generates first color image data by imaging biological tissue illuminated with the first light, using the image sensor, the storage unit stores a sensitivity ratio, which is a ratio between an imaging sensitivity for the first light and an imaging sensitivity for the second light of the image sensor, and the characteristic amount acquisition unit includes a first portion configured to acquire a first characteristic amount of the biological tissue based on a first corrected ratio obtained by using the sensitivity ratio to correct a first ratio that is sensitive to the first characteristic amount of the biological tissue, among ratios of a plurality of components of the first color image data of the biological tissue and a plurality of components of the second color image data of the biological tissue, and a second portion configured to acquire the second characteristic amount of the biological tissue based on the first characteristic amount and the second corrected ratio.

Aspect 13

The endoscope system according to Aspect 9 or 10, wherein the imaging unit generates first color image data by imaging biological tissue illuminated with the first light, using the image sensor, the storage unit stores a first light intensity ratio, which is a ratio between a light intensity of the first light and the light intensity of the second light, and a sensitivity ratio, which is a ratio between an imaging sensitivity for the first light and an imaging sensitivity for the second light of the image sensor, and the characteristic amount acquisition unit includes a first portion configured to acquire a first characteristic amount of the biological tissue based on a first corrected ratio obtained by using the sensitivity ratio and the first light intensity ratio to correct a first ratio that is sensitive to the first characteristic amount of the biological tissue, among ratios of a plurality of components of the first color image data of the biological tissue and a plurality of components of the second color image data of the biological tissue, and a second portion configured to acquire the second characteristic amount of the biological tissue based on the first characteristic amount and the second corrected ratio.

Aspect 14

The endoscope system according to Aspect 12 or 13, wherein the sensitivity ratio is a ratio set such that the value of the first corrected ratio obtained when a reference subject for which the value of the first ratio is a known reference value is imaged using the image sensor is the reference value of the reference subject.

Aspect 15

The endoscope system according to any one of Aspects 1 to 8 and Aspects 11 to 13, wherein the first characteristic amount is an amount of hemoglobin in the biological tissue, and the first ratio is a ratio between a luminance component of the second color image data and an R component or the total components of the R component and a G component of the first color image data.

Aspect 16

The endoscope system according to any one of Aspects 9 to 15, wherein the second characteristic amount is an oxygen saturation of hemoglobin in the biological tissue, and the second ratio is a ratio between a luminance component of the third color image data and a luminance component of the second color image data.

Aspect 17

The endoscope system according to any one of Aspects 9 to 16, wherein the wavelength band of the third light is included in the wavelength band of the second light.

Aspect 18

The endoscope system according to any one of Aspects 1 to 17, wherein in the wavelength band of the second light, one component of the second color image data includes a wavelength band that is sensitive to change in the amount of hemoglobin in the biological tissue but is not sensitive to change in the oxygen saturation of the hemoglobin.

Aspect 19

The endoscope system according to any one of Aspects 9 to 18, wherein in the wavelength band of the third light, one component of the third color image data includes a wavelength band that is sensitive to change in the oxygen saturation of the biological tissue.

Aspect 20

The endoscope system according to any one of Aspects 1 to 19, wherein the light source apparatus has a configuration for emitting light with different wavelength bands by sequentially switching a plurality of optical filters on an optical path.

Aspect 21

The endoscope system according to Aspect 20, wherein the second light is filtered light of the first light obtained by using one of the optical filters to transmit a first wavelength band within a range of 500 nm to 600 nm in the wavelength band of the first light, and the third light is filtered light of the first light obtained by using one of the optical filters to transmit a second wavelength band that is narrower than the first wavelength band and is within the range of the first wavelength band.

Also, the characteristic amount calculation method of the present disclosure includes the following aspects.

Aspect 22

A biological tissue characteristic amount calculation method, including:

a step of illuminating biological tissue with at least first light and second light with different wavelength bands;

a step of generating first color image data by imaging biological tissue illuminated with the first light, and generating second color image data by imaging the biological tissue illuminated with the second light, using an image sensor;

a step of generating a first corrected ratio obtained by using a pre-acquired first light intensity ratio, which is a ratio between a light intensity of the first light and a light intensity of the second light, to correct a first ratio that is sensitive to a first characteristic amount of the biological tissue, among ratios between a plurality of components of the first color image data of the biological tissue and a plurality of components of the second color image data of the biological tissue; and a step of calculating the first characteristic amount of the biological tissue based on the first corrected ratio.

Aspect 23

A biological tissue characteristic amount calculation method, including:

a step of illuminating biological tissue with at least first light and second light with different wavelength bands;

a step of generating first color image data by imaging the biological tissue illuminated with the first light using an image sensor, and generating second color image data by imaging the biological tissue illuminated with the second light;

a step of generating a first corrected ratio obtained by using a pre-acquired first light intensity ratio, which is a ratio between an imaging sensitivity for the first light and an imaging sensitivity for the second light of the image sensor, to correct a first ratio that is sensitive to a first characteristic amount of the biological tissue, among ratios between a plurality of components of the first color image data of the biological tissue and a plurality of components of the second color image data of the biological tissue; and a step of calculating the first characteristic amount of the biological tissue based on the first corrected ratio.

Aspect 24

A biological tissue characteristic amount calculation method, including:

a step of illuminating biological tissue with light having at least two light components with different wavelength bands;

a step of generating color image data by imaging the biological tissue illuminated with the light, using an image sensor;

a step of generating a first corrected ratio obtained by using a pre-acquired sensitivity ratio, which is a ratio between imaging sensitivities in different wavelength bands of the light components of the image sensor, to correct a first ratio that is sensitive to a first characteristic amount of the biological tissue, among ratios between corresponding components corresponding to wavelength bands of the light components of the color image data of the biological tissue; and a step of calculating the first characteristic amount of the biological tissue based on the first corrected ratio.

Aspect 25

A biological tissue characteristic amount calculation method, including:

a step of illuminating biological tissue with first light, second light, and third light with different wavelength bands;

a step of generating second color image data by imaging the biological tissue illuminated with the second light using an image sensor, and generating third color image data by imaging the biological tissue illuminated with the third light;

a step of generating a second corrected ratio obtained by using a pre-acquired second light intensity ratio, which is a ratio between a light intensity of the second light and a light intensity of the third light, to correct a second ratio that is sensitive to a second characteristic amount of the biological tissue, among ratios between a plurality of components of the second color image data of the biological tissue and a plurality of components of the third color image data of the biological tissue; and a step of calculating the second characteristic amount of the biological tissue based on the second corrected ratio.

Advantageous Effects of the Disclosure

According to the above-described endoscope system and characteristic amount calculation method, highly-accurate information on the characteristic amount can be obtained when the characteristic amount of the biological tissue is to be acquired from image data of the biological tissue illuminated using multiple types of light.

DESCRIPTION OF EMBODIMENTS

Hereinafter, the present embodiment will be described with reference to the drawings.

An endoscope system of an embodiment described below is a system in which biological data of biological tissue (e.g., a characteristic amount of biological tissue such as an amount of hemoglobin or an oxygen saturation) is quantitatively analyzed based on multiple pieces of color image data obtained by illuminating the biological tissue with types of light having different wavelength regions and imaging the biological tissue as an imaging subject, and the analysis result is made into an image and displayed. If the amount of hemoglobin and the oxygen saturation to be described below are to be quantified, a property is used in which the spectral characteristic of blood (i.e., the spectral characteristic of hemoglobin) continuously changes according to the amount of hemoglobin and the oxygen saturation.

In an embodiment, in order to quantify the characteristic amounts of the biological tissue (the amount of hemoglobin and the oxygen saturation), an image of the biological tissue illuminated with multiple types of illuminating light (first to third light) with different wavelength bands is obtained through imaging, and ratios (first ratio and second ratio) between components of the color image data of the biological tissue are calculated. At this time, in order to suppress variation of the characteristic amounts (the amount of hemoglobin and the oxygen saturation) of the biological tissue caused by the light intensity of the illuminating light or the imaging sensitivity of the imaging sensor varying in the endoscope system, the amount of hemoglobin or the oxygen saturation is obtained using a corrected ratio (first corrected ratio, second corrected ratio) obtained by correcting the ratio (first ratio, second ratio) between the components of the color image data of the biological tissue. Accordingly, highly-accurate information on the characteristic amount can be obtained. Note that as will be described later, the oxygen saturation is calculated based on the second corrected ratio and the calculated amount of hemoglobin, but due to the fact that the amount of hemoglobin is calculated based on the first corrected ratio, the calculation of the oxygen saturation also encompasses the oxygen saturation being calculated based on the second corrected ratio and the first corrected ratio.

Configuration of Endoscope System

Figure 1:
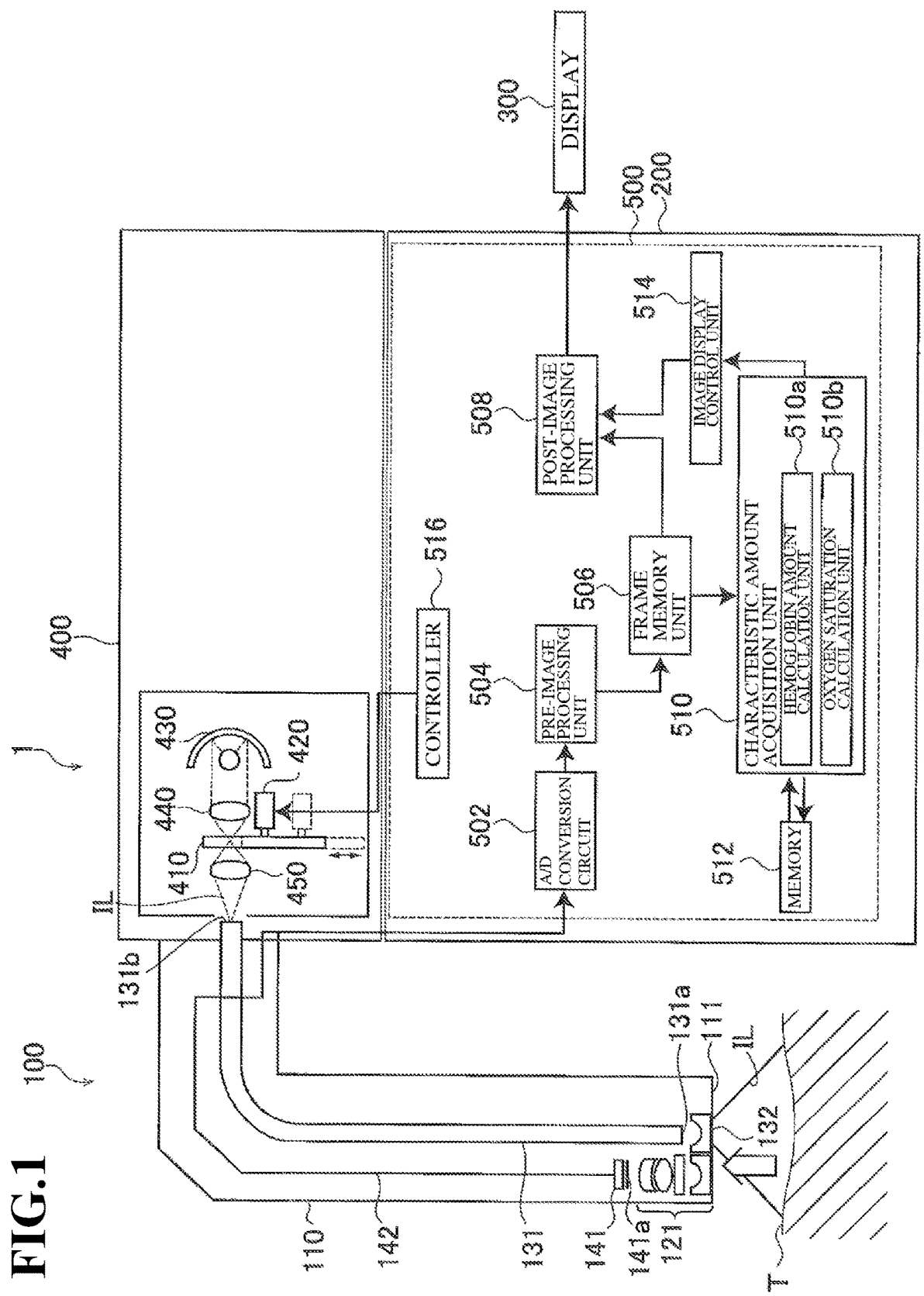
FIG. 1 is a block diagram showing a configuration of an example of an endoscope system of an embodiment.

FIG. 1 is a block diagram showing a configuration of an endoscope system 1 according to an embodiment. The endoscope system 1 includes: an electronic endoscope (endoscope) 100; a processor 200; a display 300; and a light source apparatus 400. The electronic endoscope 100 and the display 300 are detachably connected to the processor 200. Also, the processor 200 includes an image processing unit 500. The light source apparatus 400 is detachably connected to the processor 200. The light source apparatus 400 may also be incorporated in the housing of the processor 200.

The electronic endoscope 100 includes an insertion tube 110 to be inserted into the body of an examinee. A light guide 131 that extends over approximately the entire length of the insertion tube 110 is provided inside of the insertion tube 110. A leading end portion 131*a*, which is one end portion of the light guide 131, is located near the leading end portion of the insertion tube 110, or in other words, near an insertion tube leading end portion 111, and a base end portion 131*b*, which is the other end portion of the light guide 131, is located at the portion at which the light guide 131 is connected to the light source apparatus 400. Accordingly, the light guide 131 extends from the portion at which the light guide 131 is connected to the light source apparatus 400 to near the insertion tube leading end portion 111.

The light source apparatus 400 includes, as a light source, a light source lamp 430 that generates light with a large light amount, such as a xenon lamp. The light emitted from the light source apparatus 400 is incident on the base end portion 131*b* of the light guide 131 as illuminating light IL. The light incident on the base end portion 131*b* of the light guide 131 is guided through the light guide 131 to the leading end portion 131*a* and is emitted from the leading end portion 131*a*. A light distribution lens 132 that is arranged facing the leading end portion 131*a* of the light guide 131 is provided at the insertion tube leading end portion 111 of the electronic endoscope 100. The illuminating light IL emitted from the leading end portion 131*a* of the light guide 131 passes through the light distribution lens 132 and illuminates biological tissue T near the insertion tube leading end portion 111.

An object lens group 121 and an image sensor 141 are provided at the insertion tube leading end portion 111 of the electronic endoscope 100. The object lens group 121 and the image sensor 141 form an imaging unit. The light reflected or dispersed by the surface of the biological tissue T in the illuminated light IL is incident on the object lens group 121, is condensed, and forms an image on a light receiving surface of the image sensor 141. As the image sensor 141, it is possible to use a known image sensor, such as a CCD (Charge Coupled Device) image sensor or a CMOS (Complementary Metal Oxide Semiconductor) image sensor for color image imaging, with a light receiving surface provided with a color filter 141*a*.

Figure 2:
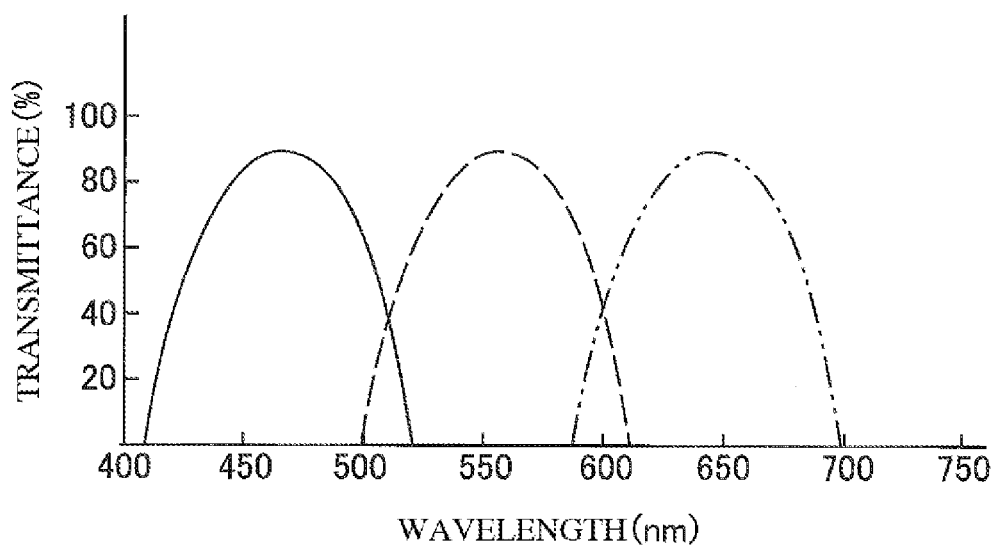
FIG. 2 is a diagram showing an example of a transmission spectrum of a color filter built into an image sensor to be used in an embodiment.

The color filter 141*a* is a so-called on-chip filter in which R color filters that allow transmission of red-colored light, G color filters that allow transmission of green-colored light, and B color filters that allow transmission of blue-colored light are arrayed and formed directly on the light-receiving elements of the image capture element 141. FIG. 2 is a diagram showing an example of spectral characteristics of red (R), green (G), and blue (B) filters of an image sensor used in an embodiment. The R color filter is a filter that allows transmission of light with a wavelength longer than a wavelength of about 570 nm (e.g., 580 nm to 700 nm), the G color filter is a filter that allows transmission of light with a wavelength of about 470 nm to 620 nm, and the B color filter is a filter that allows transmission of light with a wavelength shorter than a wavelength of about 530 nm (e.g., 420 nm to 520 nm).

The image sensor 141 is an imaging means for imaging the biological tissue T illuminated with the multiple types of light and generating color image data corresponding to the types of light, and is an image data generation means for generating color image data corresponding to the light reflected by or dispersed on the biological tissue T due to the biological tissue T being illuminated with multiple types of light with different wavelength ranges. The image sensor 141 is controlled so as to perform driving in synchronization with the image processing unit 500, which will be described later, and periodically (e.g., in intervals of 1/30 of a second) outputs the color image data corresponding to the image of the biological tissue T formed on the light receiving surface. The color image data output from the image sensor 141 is sent to the image processing unit 500 of the processor 200 via a cable 142.

The image processing unit 500 mainly includes: an A/D conversion circuit 502; a pre-image processing unit 504; a frame memory unit 506; a post-image processing unit 508; a characteristic amount acquisition unit 510; a memory 512; an image display control unit 514; and a controller 516.

The A/D conversion circuit 502 performs A/D conversion on the color image data input via the cable 142 from the image sensor 141 of the electronic endoscope 100 and outputs digital image data. The digital data output from the A/D conversion circuit 502 is sent to the pre-image processing unit 504.

The pre-image processing unit 504 uses the digital data to generate color image data of R, G, and B components that form an image, through demosaic processing from R digital image data imaged by the light receiving elements in the image sensor 141 on which the R color filters are mounted, G digital image data imaged by the light receiving elements in the image sensor 141 on which the G color filters are mounted, and B digital image data imaged by the light receiving elements in the image sensor 141 on which the B color filters are mounted. Furthermore, the pre-image processing unit 504 is a portion that implements predetermined signal processing such as color correction, matrix operation, and white balance correction on the color image data of the generated R, G, and B components.

The frame memory unit 506 temporarily stores color image data of each image that was imaged by the image sensor 141 and subjected to signal processing.

The post-image processing unit 508 generates screen data for display on a display by reading out the color image data stored in the frame memory unit 506 or performing signal processing (γ (gamma) correction, etc.) on the image data generated by a later-described image display control unit 514. As will be described later, the image data generated by the image display control unit 514 includes the data of the distribution image of the characteristic amount such as the oxygen saturation of the hemoglobin in the biological tissue T. The generated image data (video format signal) is output to the display 300. Accordingly, an image of the biological tissue T, a distribution image of the characteristic amount of the biological tissue T, and the like are displayed on the screen of the display 300.

In response to an instruction from the controller 516, as will be described later, the characteristic amount acquisition unit 510 calculates a characteristic amount of the imaged biological tissue T, such as the amount of hemoglobin, or the amount of hemoglobin and the oxygen saturation of the hemoglobin, and generates image data of a distribution image on the captured image of the imaged biological tissue T.

The characteristic amount acquisition unit 510 calculates the characteristic amounts by performing calculation using the color image data of the biological tissue T illuminated with multiple types of light with different wavelength bands, and therefore the color image data and various types of information to be used by the characteristic amount acquisition unit 510 are called from the frame memory unit 506 or the memory 512.

The image display control unit 514 controls the mode of displaying the distribution image on the captured image of the biological tissue T, the distribution image being for the characteristic amount calculated by the characteristic amount acquisition unit 510, according to an instruction from the controller 516. For example, the image display control unit 514 performs control such that the distribution image for the characteristic amount is overlaid on the captured image of the biological tissue T.

The controller 516 is a portion that, in addition to performing operation instruction and operation control for the portions of the image processing unit 500, performs operation instruction and operation control of the portions of the electronic endoscope 100 including the light source apparatus 400 and the image sensor 141.

Note that the characteristic amount acquisition unit 510 and the image display control unit 514 may be constituted by a software module that carries out the above-described functions by starting up and executing a program in a computer, and may be constituted by hardware.

In this manner, the processor 200 includes both a function of processing the color image data output from the image sensor 141 of the electronic endoscope 100 and a function of instructing and controlling operation of the electronic endoscope 100, the light source apparatus 400, and the display 300.

The light source apparatus 400 is a light emitting means for emitting first light, second light, and third light, which have different wavelength bands, and causes the first light, the second light, and the third light to be incident on the light guide 131. The light source apparatus 400 of the present embodiment emits the first light, the second light, and the third light, which have different wavelength bands, but the light source apparatus 400 may also emit four or more types of light. In this case, the fourth light may be light with the same wavelength band as the first light. In addition to the light source lamp 430, the light source apparatus 400 includes: a light condensing lens 440; a rotating filter 410; a filter control unit 420; and a light condensing lens 450. The light, which is approximately parallel light and is emitted from the light source lamp 430, is white light, for example, and is condensed by the light condensing lens 440, passes through the rotating filter 410, and thereafter is once again condensed by the light condensing lens 450 and is incident on the base end 131b of the light guide 131. Note that the rotating filter 410 can move between a position on the light path of the light irradiated from the light source lamp 430 to a retracted position off of the light path due to a moving mechanism (not shown), such as a linear guideway. Since the rotating filter 410 includes multiple filters with different transmisison transmission characteristics, the wavelength band of the light emitted from the light source apparatus 400 differs depending on the type of the rotating filter 410 that crosses the light path of the light irradiated from the light source lamp 430.

Note that the configuration of the light source apparatus 400 is not limited to that shown in FIG. 1. For example, a lamp that generates convergent light instead of parallel light may also be employed as the light source lamp 430. In this case, for example, a configuration may be used in which the light irradiated from the light source lamp 430 is condensed in front of the condensing lens 440 and the light is incident on the light condensing lens 440 as diffused light. Also, a configuration may be used in which the light condensing lens 440 is not used and approximately parallel light generated by the light source lamp 430 is directly incident on the rotating filter 410. Also, in the case of using a lamp that generates convergent light, a configuration may be used in which a collimator lens is used instead of the light condensing lens 440 and the light is incident on the rotating filter 410 in an approximately parallel state. For example, in the case of using an interference-type optical filter such as a multi-layered dielectric filter as the rotating filter 410, the approximately parallel light is incident on the rotating filter 410, whereby the incidence angle of the light on the optical filter is made uniform, and thus a more preferable filter characteristic can be obtained. Also, a lamp that generates diffused light may also be employed as the light source lamp 430. In this case as well, a configuration can be used in which a collimator lens is used instead of the light condensing lens 440 and the light is incident on the rotating filter 410 in an approximately parallel state.

Also, although the light source apparatus 400 is configured to emit multiple types of light with different wavelength bands by causing the light irradiated from the one light source lamp 430 to pass through the optical filter, a semiconductor light source such as a light-emitting diode or a laser element that outputs laser light, for example, can also be used as a light source apparatus 400, instead of the light source lamp 430. In this case, the rotating filter 410 need not be used. Also, for example, the light source apparatus 400 can also be configured to separately emit white light including excitation light with a predetermined wavelength band and fluorescent light that is excited to emit light by the excitation light, and light with a predetermined narrow wavelength band.

The configuration of the light source apparatus 400 is not particularly limited, as long as multiple types of light with different wavelength bands are emitted.

Although the light source apparatus 400 is an external apparatus attached to the electronic endoscope 100, if the light source apparatus 400 is constituted by a small light source such as a laser element, the light source apparatus 400 may be provided on the insertion tube leading end portion 111 of the electronic endoscope 100. In this case, the need for the light guide 131 is eliminated.

The rotating filter 410 is a circular disk-shaped optical unit including multiple optical filters, and is configured such that the transmission wavelength region is switched according to the rotation angle. The rotating filter 410 includes three optical filters with different transmission wavelength bands, but the rotating filter 410 may include four, five, six, or more optical filters. The rotation angle of the rotating filter 410 is controlled by the filter control unit 420 connected to the controller 516. Due to the controller 516 controlling the rotation angle of the rotating filter 410 via the filter control unit 420, the wavelength band of the illuminating light IL supplied to the light guide 131 is switched by passing through the rotating filter 410.

Figure 3:
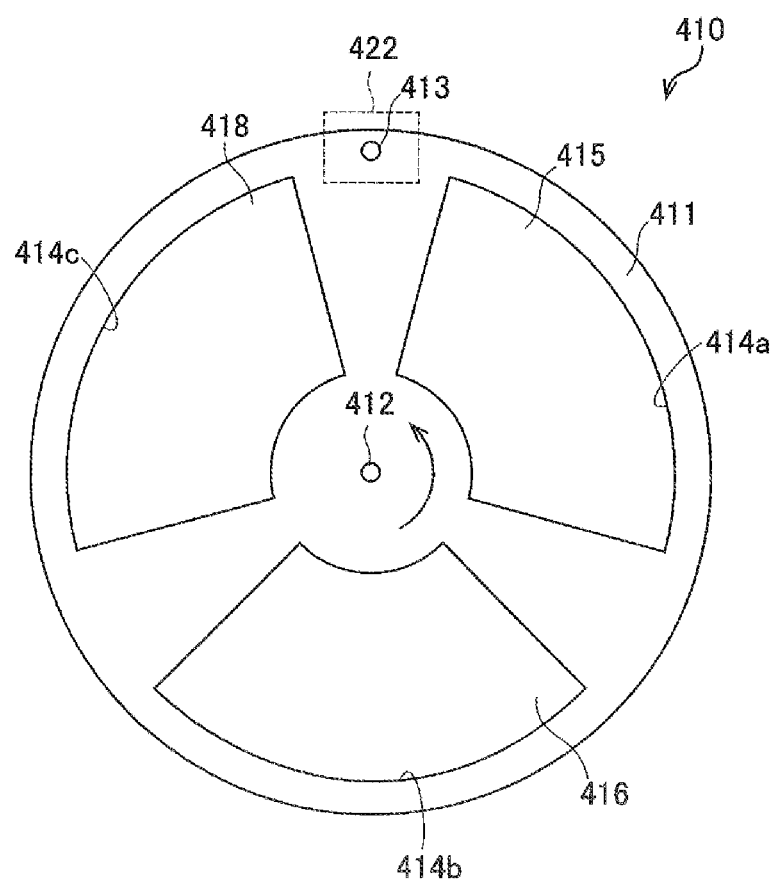
FIG. 3 is an external view of a rotating filter to be used in an embodiment.

FIG. 3 is an external view (front view) of the rotating filter 410. The rotating filter 410 includes: an approximately circular disk-shaped frame 411; and three fan-shaped optical filters 415, 416, and 418. Three fan-shaped windows 414a, 414b, and 414c are formed at an equal interval around the central axis of the frame 411, and the optical filters 415, 416, and 418 are fit into the respective windows 414a, 414b, and 414c. Note that the optical filters are all multilayered dielectric filters, but another type of optical filter (e.g., an absorption-type optical filter or an etalon filter in which a dielectric multilayer film is used as a reflection film, etc.) may also be used.

Also, a boss hole 412 is formed on the central axis of the frame 411. An output shaft of a servo motor (not shown) included in the filter control unit 420 is fixed by being inserted into the boss hole 412 and the rotating filter 410 rotates along with the output shaft of the servo motor.

When the rotating filter 410 rotates in the direction indicated by the arrow in FIG. 3, the optical filters on which the light is incident switch in the following order: optical filters 415, 416, and 418, and thereby the wavelength bands of the illuminating light IL passing through the rotating filter are sequentially switched.

Figure 4:
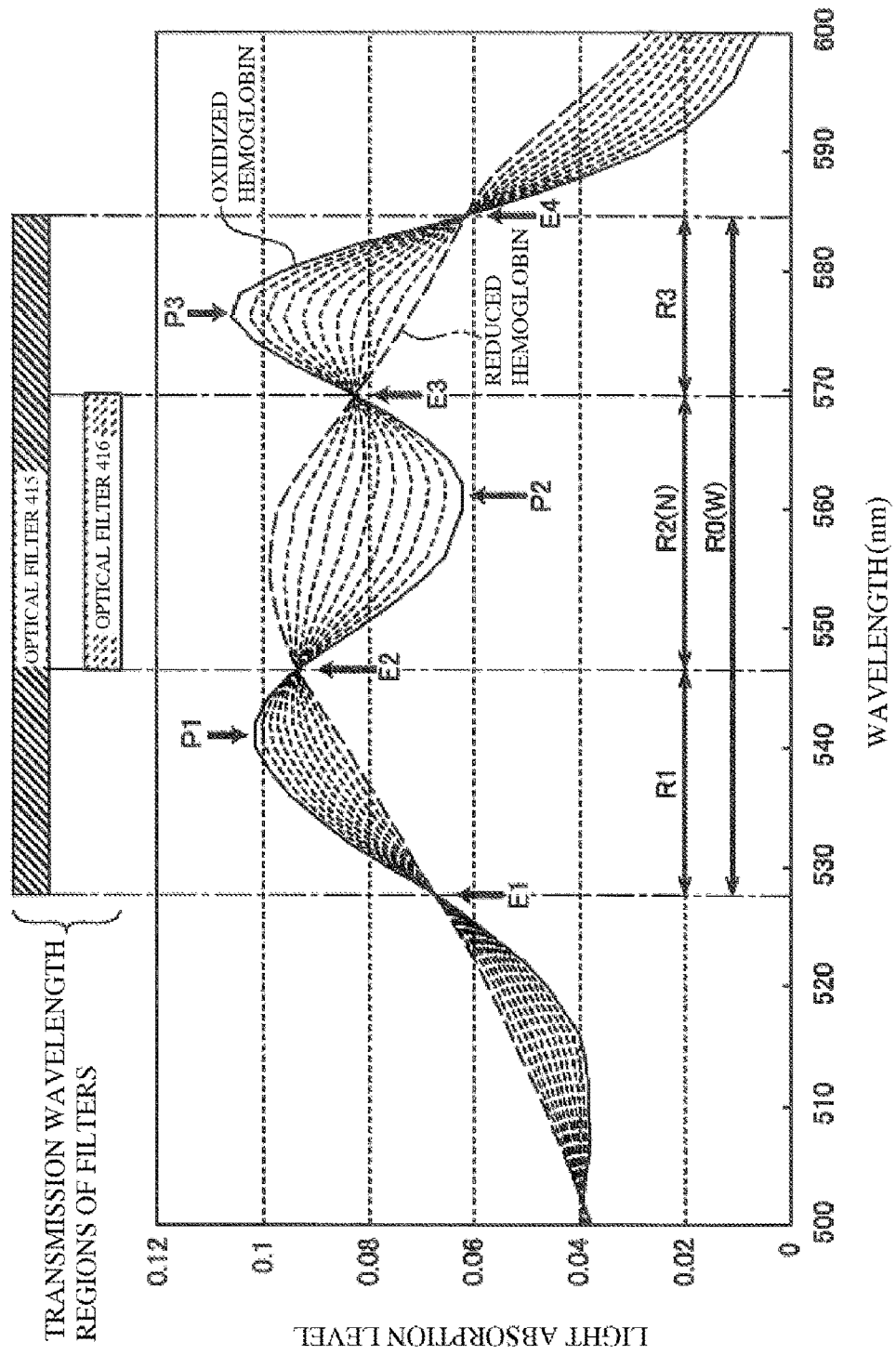
FIG. 4 is a diagram showing an example of an absorption spectrum of hemoglobin near 550 nm.

The optical filters 415 and 416 are optical band-pass filters that selectively allow transmission of light in the 550-nm band. As shown in FIG. 4, the optical filter 415 is configured to allow transmission with low loss of light in a wavelength band R0 (W band) from the isosbestic points E1 to E4, and to block light of other wavelength regions. Also, the optical filter 416 is configured to allow transmission with low loss of light in the wavelength band R2 (N band) from the isosbestic point E2 to the isosbestic point E3, and to block light of other wavelength regions.

Also, the optical filter 418 is an ultraviolet-cutting filter, and in the visible light wavelength region, the light emitted from the light source lamp 430 passes through the optical filter 418. The light that has passed through the optical filter 418 is used as white light to capture a normal observation image. Note that it is also possible to use a configuration in which the optical filter 418 is not used and the window 414c of the frame 411 is open.

Accordingly, the light that has passed through the optical filter 415 among the light irradiated from the light source lamp 430 is referred to hereinafter as "wide light", the light that has passed through the optical filter 416 among the light irradiated from the light source lamp 430 is referred to hereinafter as "narrow light", and light that has passed through the optical filter 418 among the light irradiated from the light source lamp 430 is referred to hereinafter as "white light WL".

As shown in FIG. 4, the wavelength band R1 is a band in which the peak wavelength of an absorption peak P1 originating from oxidized hemoglobin is included, the wavelength band R2 is a band in which the peak wavelength of an absorption peak P2 originating from reduced hemoglobin is included, and the wavelength band R3 is a band in which the peak wavelength of an absorption peak P3 originating from oxidized hemoglobin is included. Also, the peak wavelengths of the three absorption peaks P1, P2, and P3 are included in the wavelength region R0. FIG. 4 is a diagram showing an example of an absorption spectrum of hemoglobin near 550 nm.

Also, the wavelength band R0 of the optical filter 415 and the wavelength band R2 of the optical filter 416 are included in the transmission wavelength region (FIG. 2) of the G color filter of the color filter 141a. Accordingly, images of the biological tissue T formed by light that has passed through the optical filters 415 and 416 are obtained as images of the G component of the color image data captured by the image sensor 141. Note that the transmittances and opening sizes of the optical filter 415 and the optical filter 418 are adjusted such that the light intensity of the wide light generated from the optical filter 415 and the light intensity of the white light WL generated from the optical filter 418 are approximately the same degree. The light intensity of the wide light and the light intensity of the narrow light are different.

A through hole 413 is formed on the circumferential edge portion of the frame 411. The through hole 413 is formed at the same position (phase) as the boundary portion between the window 414a and the window 414c in the rotation direction of the frame 411. A photointerrupter 422 for detecting the through hole 413 is arranged on the periphery of the frame 411 so as to surround part of the circumferential edge portion of the frame 411. The photointerrupter 422 is connected to the filter control unit 420.

Thus, it is preferable to have a configuration in which the light source apparatus 400 emits types of light with different wavelength bands, that is, the wide light, the narrow light, and the white light WL, as the illuminating light IL by sequentially switching the multiple optical filters 415, 416, and 418 on the light path of the light irradiated by the light source lamp 430.

Calculation of Characteristic Amount of Biological Tissue

A characteristic amount of the biological tissue T is calculated by the characteristic amount acquisition unit 510 of the image processing unit 500. Processing for calculating the amount of hemoglobin and the oxygen saturation Sat of the hemoglobin in the biological tissue T as the characteristic amounts from a captured image of the biological tissue T will be described below.

As shown in FIG. 4, hemoglobin has strong absorption bands called Q bands, which originate from porphyrin, near 550 nm. The absorption spectrum of hemoglobin changes according to the oxygen saturation Sat, which indicates the percentage of oxidized hemoglobin HbO in all of the hemoglobin. The waveform with the solid line in FIG. 4 is the absorption spectrum of an oxygen saturation Sat of 100%, that is, oxidized hemoglobin HbO, and the waveform with the long broken line is the absorption spectrum of an oxygen saturation Sat of 0%, that is, reduced hemoglobin Hb. Also, the short broken lines are the absorption spectra of hemoglobin with intermediate oxygen saturations Sat of 10%, 20%, 30%, . . . and 90%, that is, a mixture of oxidized hemoglobin HbO and reduced hemoglobin Hb.

As shown in FIG. 4, in the Q band, the oxidized hemoglobin HbO and the reduced hemoglobin Hb have mutually different peak wavelengths. Specifically, the oxidized hemoglobin HbO has an absorption peak P1 near the wavelength 542 nm and an absorption peak P3 near the wavelength 576 nm. On the other hand, the reduced hemoglobin Hb has an absorption peak P2 near 556 nm. Since FIG. 4 shows absorption spectra in the case where the sum of the concentrations of the oxidized hemoglobin HbO and the reduced hemoglobin Hb is constant, isosbestic points E1, E2, E3, and E4, at which the light absorption degree is constant regardless of the proportion of the oxidized hemoglobin HbO and the reduced hemoglobin Hb, that is, regardless of the oxygen saturation, appear. The wavelength band interposed between the isosbestic points E1 and E2 is the wavelength band R1, which was described above for the optical filter 410, the wavelength band interposed between the isosbestic points E2 and E3 is the wavelength band R2, the wavelength band interposed between the isosbestic points E3 and E4 is the wavelength band R3, and the wavelength band interposed between the isosbestic points E1 and E4, that is, the band obtained by combining the wavelength bands R1, R2, and R3, is the wavelength band R0. Accordingly, the wavelength band of the wide light, which is the transmission light that passed through the optical filter 415 among the light irradiated from the light source lamp 430, is the wavelength band R0, and the wavelength band of the narrow light, which is the transmission light that passed through the optical filter 416 among the light irradiated from the light source lamp 430, is the wavelength band R2.

As shown in FIG. 4, in the wavelength bands R1, R2, and R3, the absorption of the hemoglobin increases or decreases linearly with respect to the oxygen saturation. Specifically, absorptions AR1 and AR3 of the hemoglobin in the wavelength bands R1 and R3 linearly increase with respect to the concentration of the oxidized hemoglobin, that is, the oxygen saturation. Also, the absorption AR2 of the hemoglobin in the wavelength band R2 increases linearly with respect to the concentration of the reduced hemoglobin.

Here, the oxygen saturation is defined using the following equation (1).

Equation (1)

$$Sat = \frac{[HbO]}{[Hb]+[HbO]} \quad \text{Equation 1}$$

where
Sat: oxygen saturation
[Hb]: Concentration of reduced hemoglobin
[HbO]: Concentration of oxidized hemoglobin
[Hb]+[HbO]: Amount of hemoglobin (tHb)

Also, equation (2) and equation (3), which indicate the concentrations of the oxidized hemoglobin HbO and the reduced hemoglobin Hb, are obtained using equation (1).

Equation (2):

$$[HbO]=Sat \cdot ([Hb]+[HbO]) \quad \text{Equation 2}$$

Equation (3):

$$[Hb]=(1-Sat) \cdot ([Hb]+[HbO]) \quad \text{Equation 3}$$

Accordingly, the absorptions AR1, AR2, and AR3 of the hemoglobin are characteristic amounts that depend on both the oxygen saturation and the amount of hemoglobin.

Here, it is evident that the total value of the light absorption level in the wavelength band R0 is a value that does not depend on the oxygen saturation Sat and is determined by the amount of hemoglobin. Accordingly, the amount of hemoglobin can be quantified based on the total value of the light absorption level in the wavelength band R0. Also, the oxygen saturation Sat can be quantified based on the total value of the light absorption levels in the wavelength band R1, the wavelength band R2, or the wavelength band R3, and the amount of hemoglobin quantified based on the total value of the wavelength band R0.

The characteristic amount acquisition unit 510 includes: a hemoglobin amount calculation unit (first portion) 510a that calculates and acquires the amount of hemoglobin in the biological tissue T based on a later-described first ratio that is sensitive to change in the amount of hemoglobin (first characteristic amount) of the biological tissue T; and an oxygen saturation calculation unit (second portion) 510b that calculates and acquires the oxygen saturation of the hemoglobin in the biological tissue T based on a later-described second ratio that is sensitive to change in the calculated amount of hemoglobin (first characteristic amount) and the oxygen saturation of the hemoglobin (second characteristic amount). The first ratio or the second ratio being sensitive to change in the amount of the hemoglobin or change in the oxygen saturation means that the first ratio or the second ratio changes with respect to change in the amount of hemoglobin or change in the oxygen saturation.

Due to the fact that the value of the luminance component of the color image data of the biological tissue T illuminated with the wide light (the light in the wavelength band R0 that passed through the optical filter 415) corresponds to the total value of the light absorption levels in the above-described wavelength band R0, the hemoglobin amount calculation unit 510a of the characteristic amount acquisition unit 510 of the present embodiment calculates the amount of hemoglobin based on the luminance component of the color image data in the wavelength band R0. Here, the luminance component can be calculated by multiplying a predetermined coefficient by the R component of the color image data, multiplying a predetermined coefficient by the G component of the color image data, multiplying a predetermined coefficient by the value of the B component of the color image data, and adding together the multiplication results.

Specifically, the hemoglobin amount calculation unit 510a of the characteristic amount acquisition unit 510 calculates the amount of hemoglobin based on a ratio Wide(Yh)/WL(R) or Wide(Yh)/{WL(R)+WL(G)} (first ratio) obtained by dividing the luminance component Wide (Yh) of the color image data (second color image data) of the biological tissue T in which the wide light (second light) is used as the illuminating light IL, by an R component WL(R) or a total component WL(R)+WL(G) of the R component WL(R) and a G component WL(G) of the color image data (first color image data) of the biological tissue T in which the white light WL (first light) is used as the illuminating light IL. The ratio Wide(Yh)/WL(R) or Wide(Yh)/{WL(R)+WL(G)} obtained by dividing the luminance component Wide (Yh) by WL(R) or {WL(R)+WL(G)} is used in the calculation of the amount of hemoglobin in order to cancel out changes in the spectral characteristic of the biological tissue T according to the degree to which the illuminating light IL is diffused by the surface of the biological tissue T. In particular, the reflection spectrum of biological tissue T of the inner wall of a digestive organ or the like is easily influenced by the wavelength property of the diffusion of the illuminating light by the biological tissue T, in addition to the wavelength property (specifically, the absorption spectrum property of the oxidized hemoglobin and the reduced hemoglobin) of the absorption by the components constituting the biological tissue T. The R component WL(R) or the total component WL(R)+WL(G) of the R component and the G component of the color image data (first color image data) of the biological tissue T in which the white light WL (first light) is used as the illuminating light IL is not influenced by the amount of hemoglobin and the oxygen saturation Sat and indicates the degree of diffusion of the biological tissue T of the illuminating light IL. Accordingly, in order to cancel out the influence of the diffusion of the biological tissue T of the illuminating light IL from the reflection spectrum of the biological tissue T, the wavelength band of the white light WL (reference light) is preferably set such that one component of the first color image data includes a wavelength band that is not sensitive to change in the amount of hemoglobin in the biological tissue T. In addition to this, the wavelength band of the white light WL (reference light) is preferably set such that one component of the first color image data includes a wavelength band that is not sensitive to change in the oxygen saturation.

In the embodiment, a reference table, which indicates the correlation between information of the above-described first ratio (more accurately, the later-described first corrected ratio) and the amount of hemoglobin in the biological tissue T with a known amount of hemoglobin, is stored in the memory 512 in advance, and the hemoglobin amount calculation unit 510a of the characteristic amount acquisition unit 510 uses the reference table to calculate the amount of hemoglobin based on the above-described first ratio in the color image data obtained by imaging the biological tissue T.

In the calculation of the amount of hemoglobin, it is preferable to use, as the first ratio, a ratio Wide(Yh)/WL(R) or Wide(Yh)/{WL(R)+WL(G)} of the luminance component Wide(Yh) of the color image data (second color image data) of the biological tissue T in which the wide light (second light) is used as the illuminating light IL and the R component WL(R) or the total components WL(R)+WL(G) of the R component and the G component of the color image data (first color image data) of the biological tissue T in which the white light WL (first light) is used as the illuminating light IL, but it is also preferable to use the G component Wide(G) instead of the luminance component Wide(Yh) of the color image data (second color image data) of the biological tissue T in which the wide light (second light) is used as the illuminating light IL.

Furthermore, as described above, due to the fact that the total value of the light absorption level in the wavelength band R2 decreases along with an increase in the oxygen saturation Sat, and that the total value of the light absorption level in the wavelength band R0 changes according to the amount of hemoglobin but is constant regardless of change in the oxygen saturation Sat, the oxygen saturation calculation unit 510b of the characteristic amount acquisition unit 510 calculates the oxygen saturation based on the second ratio determined below. That is, the oxygen saturation calculation unit 510b of the characteristic amount acquisition unit 510 calculates, as the second ratio, a ratio Narrow(Yh)/Wide(Yh) of the luminance component Narrow(Yh) of the color image data (third color image data) of the biological tissue illuminated with the narrow light, which is the light in the wavelength band R2 that passed through the optical filter 416, and the luminance component Wide(Yh) of the color image data (second color image data) of the biological tissue T illuminated with the wide light (the light in the wavelength band R0 that passed through the optical filter 416). On the other hand, a correlation indicating the relationship between the amount of hemoglobin, the lower limit value of the second ratio at which the oxygen saturation Sat=0%, and the upper limit value of the second ratio Narrow(Yh)/Wide(Yh) at which the oxygen saturation Sat=100% is obtained from a known sample and stored in advance in the memory 512. The oxygen saturation calculation unit 510b of the characteristic amount acquisition unit 510 obtains the lower limit value and the upper limit value of the second ratio using the above-described correlation and the calculation result of the amount of hemoglobin obtained from the color image data generated by imaging the biological tissue T, and calculates the position in the range between the upper limit value and the lower limit value at which the value of the second ratio Narrow(Yh)/Wide(Yh) of the imaged biological tissue T is located, in consideration of the fact that the oxygen saturation Sat changes linearly according to the second ratio between the obtained lower limit value and the upper limit value. In this manner, the oxygen saturation calculation unit 510b of the characteristic amount acquisition unit 510 calculates the oxygen saturation Sat.

Also, a reference table indicating the amount of hemoglobin and a correlation between the information on the second ratio (more accurately, a later-described second corrected ratio) and an oxygen saturation Sat of the hemoglobin can be obtained based on a known sample and can be stored in the memory 512 in advance, and the oxygen saturation Sat of the hemoglobin can also be calculated based on the calculated second ratio by referencing the reference table.

In one embodiment, the second ratio is used as a ratio between the luminance component Narrow(Yh) of the color image data (third color image data) of the biological tissue T illuminated with the narrow light and the luminance component Wide(Yh) of the color image data (second color image data) of the biological tissue T illuminated with the wide light, but it is also possible to use the ratio between the G component Narrow(G) of the color image data (third color image data) of the biological tissue T illuminated with the narrow light and the G component Wide(G) of the color image data (second color image data) of the biological tissue T illuminated with the wide light.

Also, in an embodiment, in order to calculate the second ratio, the narrow light in the wavelength band R2 is used to illuminate the biological tissue T, but there is no limitation to the narrow light. For example, it is also possible to use light whose wavelength band is the wavelength band R1 or the wavelength band R2, with the intention of using the wavelength band R1 or the wavelength band R2 in which the total value of the light absorption level changes with respect to change in the oxygen saturation Sat. In this case, the filter characteristic of the optical filter 416 is preferably set to the wavelength band R1 or the wavelength band R2.

Thus, it is preferable that the wavelength band of the narrow light (third light) is included in the wavelength band of the wide light (second light) in order to accurately calculate the oxygen saturation Sat. Also, in light of the fact that the oxygen saturation Sat can be calculated accurately, the wavelength band of the wide light (second light) is preferably set such that one component of the second color image data, such as the luminance component or G component, includes the wavelength band R0, which is sensitive to change in the amount of hemoglobin but is not sensitive to change in the oxygen saturation. In light of the fact that the oxygen saturation Sat can be calculated accurately, the wavelength band of the narrow light (third light) is set such that one component of the third color data, such as the luminance component or the G component, includes the wavelength band R2, which is sensitive to change in the oxygen saturation Sat of the biological tissue T.

Also, it is preferable that the above-described wide light (second light) is filtered white light WL (first light) obtained by allowing the first wavelength band in the region from 500 nm to 600 nm, for example, the wavelength band between the isosbestic point E1 and the isosbestic point E4, in the wavelength band of the white light WL (first light) to pass through one optical filter, and the narrow light (third light) is filtered light of the white light WL (first light) obtained by allowing a second wavelength band that is narrower than the first wavelength band in the range of the first wavelength band, such as the wavelength band between the isosbestic point E2 and the isosbestic point E3, to pass through one optical filter. For example, the first wavelength band is preferably a band in the range of 510 nm to 590 nm. Also, for example, the second wavelength band is preferably a band in the region of 510 nm to 590 nm, and is more preferably a band in the region of 530 nm to 580 nm.

Also, in the above-described embodiment, when the amount and the oxygen saturation Sat of the hemoglobin are calculated using the light absorption level of the hemoglobin, the light in the wavelength band near 550 nm is used as the illuminating light as shown in FIG. 4, but there is no limitation to this frequency band. In the light absorption level of the hemoglobin, outside of the wavelength band near 550 nm as well, a large absorption peak exists at 420 to 450 nm and includes isosbestic points. In the periphery of the isosbestic points, the waveforms of the absorption spectra of the oxidized hemoglobin and the reduced hemoglobin switch alternatingly. For this reason, in an embodiment, it is also preferable that the hemoglobin amount and the oxygen saturation are calculated using light with different wavelengths or wavelength bands in the wavelength band of 400 to 460 nm as the illuminating light. In this case as well, in the calculation of the hemoglobin amount and the oxygen saturation, as will be described later, the first ratio and the second ratio can be corrected using a first light intensity ratio G1, a sensitivity ratio G2, and a second light intensity ratio G3, which will be described later.

In the above-described embodiment, when the amount of hemoglobin and oxygen saturation Sat are to be obtained, three types of light with different wavelength bands are used as the illuminating light. However, according to an embodiment, in order to obtain the amount of hemoglobin and the oxygen saturation Sat, it is also preferable that the light source apparatus 400 emits, as the illuminating light, first light including two light components with mutually different wavelength bands, and second light with another wavelength band that is different from the two wavelength bands of the above-described light components. In this case, the hemoglobin amount calculation unit 510a can obtain the first correction ratio by using the later-described sensitivity ratio G2 to correct the first ratio obtained based on the ratio between the component a and the component b, which are corresponding components corresponding to the two wavelength bands extracted from the color image data generated when the first light is used as the illuminating light. The above-described component a and the component b are extracted by performing a matrix operation on a component of the color image data in the pre-image processing unit 504 shown in FIG. 1.

For example, a light component (red light component) in the wavelength band of 620 to 670 nm, and a light component (green light component) in the wavelength band of 525 to 582 nm are included in the first light. The wavelength band of the second light is 545 to 570 nm. In this case, according to the embodiment, the first ratio, which is to be an index for obtaining the amount of hemoglobin, can be set as a ratio of the corresponding component corresponding to the green light component (component in the wavelength band of 525 to 582 nm) among the corresponding components, with respect to the sum of the corresponding component corresponding to the green light component (component in the wavelength band of 525 to 582 nm) and the corresponding component corresponding to the red light component (component in the wavelength band of 620 to 670 nm), that is, to the composite corresponding component. The second ratio, which is to be an index for obtaining the oxygen saturation Sat, can be set as a ratio of the component corresponding to the wavelength band of 545 to 570 nm of the color image data corresponding to the second light, with respect to the corresponding component corresponding to the green light component (component in the wavelength band of 525 to 582 nm) of the color image data corresponding to the first light.

Also, according to the embodiment, it is also possible to obtain the hemoglobin amount and the oxygen saturation Sat using the component of the color image data by obtaining one piece of color image data using one type of light having three light components, instead of the three types of light to be used as the illuminating light. In this case, one type of light is used as the illuminating light, and therefore since the configuration of the light source apparatus 400 is simplified and there is no need to generate the multiple pieces of color image data, the configuration of the portions of the processor 200 is simplified.

In this case, the hemoglobin amount calculation unit 510a can obtain the first correction ratio by using the later-described sensitivity ratio G1 to correct the first ratio obtained based on the ratio between the component a and the component b, which are corresponding components corresponding to the two wavelength bands extracted from the color image data generated when the first light is used as the illuminating light.

For example, a light component (blue light component) in the wavelength band of 450 to 500 nm, a light component (green light component) in the wavelength band of 525 to 582 nm, and a light component (red light component) in the wavelength band of 620 to 670 nm are included in one type of light. The three corresponding components of the color image data corresponding to the above-described wavelength bands can be obtained due to the color image data obtained with this type of light being subjected to a matrix operation by the pre-image processing unit 504 shown in FIG. 1. In this case, according to an embodiment, the first ratio, which is to be an index for obtaining an amount of hemoglobin, can be set to a ratio of the corresponding component corresponding to the green light component (component with a wavelength band of 525 to 582 nm), with respect to a composite corresponding component obtained based on the three corresponding components (e.g., the corresponding component having a value obtained by finding a weighted average of three corresponding components). Furthermore, the second ratio that is to be an index for obtaining the oxygen saturation Sat can be set to a ratio of the corresponding component corresponding to the blue light component (component with the wavelength band of 450 to 500 nm), with respect to the corresponding component corresponding to the green light component (component with the wavelength band of 525 to 582 nm).

Hereinafter, correction of the first ratio and the second ratio will be described based on an embodiment in which the white light WL (first light), wide light (second light), and the narrow light (third light) are used as the illuminating light.

Correction of First Ratio: Light Intensity

In the above-described embodiment, the amount of hemoglobin in the biological tissue T is calculated based on the ratio Wide(Yh)/WL(R) or Wide(Yh)/{WL(R)+WL(G)}, which is the first ratio between components of the color image data of the captured image of the biological tissue T illuminated with the white light WL (first light) and the wide light (second light), which have different wavelength bands, and therefore in order to calculate a reliable amount of hemoglobin, it is preferable that the ratio of the light intensities of the two types of light with different wavelength bands is a predetermined value, that is, that the ratio of the light intensities is constant without variation between multiple endoscope systems. However, the ratio between the light intensity of the white light WL (first light) and the light intensity of the wide light (second light) slightly varies in some cases due to manufacturing error or the like in each endoscope system. For this reason, the amount of hemoglobin calculated based on the first ratio Wide(Yh)/WL(R) or Wide(Yh)/{WL(R)+WL(G)} tends to vary between multiple endoscope systems. In this case, variation in the calculation results of the hemoglobin between endoscope systems can be suppressed by correcting the reference table used to calculate the amount of hemoglobin, so as to match the variation of the light intensity of the white light WL (first light) and the light intensity of the wide light (second light). However, it is complicated to re-create the reference table for each endoscope system. For this reason, the hemoglobin amount calculation unit 510a of the characteristic amount acquisition unit 510 corrects the ratio Wide(Yh)/WL(R) or Wide(Yh)/{WL(R)+WL(G)}, which is the first ratio. Specifically, the first light intensity ratio G1, which is the ratio between the light intensity of the white light WL (first light) and the light intensity of the wide light (second light) is measured in advance, and the measurement result is stored in the memory 512. When the amount of hemoglobin is to be calculated using the first ratio, the hemoglobin amount calculation unit 510a uses, as information on the first ratio, a first corrected ratio Wide(Yh)/{WL(R)·G1} or Wide(Yh)/[{WL(R)+WL(G)}·G1] obtained by using the first light intensity ratio G1 to correct (divide) the ratio Wide(Yh)/WL(R) or Wide(Yh)/{WL(R)+WL(G)}, which is the first ratio, and calculates and acquires the amount of hemoglobin in the biological tissue T (first characteristic amount) using the reference table, based on the first corrected ratio. Note that the ratio Wide(Yh)/WL(R) or Wide(Yh)/{WL(R)+WL(G)} is a parameter that is sensitive to the amount of hemoglobin. Being sensitive means that when the amount of hemoglobin changes, the ratio Wide(Yh)/WL(R) or Wide(Yh)/{WL(R)+WL(G)} also changes in accordance with the change.

As described above, the amount of hemoglobin is calculated based on the first corrected ratio Wide(Yh)/{WL(R)·G1} or Wide(Yh)/[{WL(R)+WL(G)}·G1], and therefore the result of calculating the amount of hemoglobin is the same even if the ratio between the light intensity of the white light WL (first light) and the light intensity of the wide light (second light) varies between endoscope systems. With the light source apparatus 400, the white light WL and the wide light are transmission light that has passed through the optical filters 415 and 418 in the light irradiated from the first light source lamp 430, and therefore the variation in the ratio between the light intensity of the white light WL (first light) and the light intensity of the wide light (second light intensity) is caused by variation in the light transmittance of the optical filter 415 and the light transmittance of the optical filter 418 and variation in the sizes (opening sizes) of a window 414a and a window 414c of the rotating filter 410.

The first light intensity ratio G1 stored in the memory 512 is preferably the ratio of a component of the color image data of a reference subject generated by imaging the reference subject illuminated with the white light WL (first light) and the wide light (second light) using the image sensor 141 or a reference image sensor, or a value obtained by multiplying this ratio by a constant. More specifically, the first light intensity ratio G1 is a value obtained by dividing the value of a component of the color image data of the reference subject generated by imaging the reference subject illuminated with the wide light (second light) using the image sensor 141 or a reference image sensor, by the value of a component of the color image data of the reference subject generated by imaging the reference subject illuminated with the white light WL (first light) using the image sensor 141 or the reference image sensor, or a value obtained by multiplying this value by a constant.

Thus, according to the embodiment, the first light intensity ratio G1 is a coefficient that corrects the first ratio such that the value of the first ratio is the value of the first ratio obtained based on components of the color image data corresponding to the white light WL and the wide light with a pre-determined light intensity, even if the light intensities of the white light WL (first light) and the wide light (second light) vary. For example, if the value of the component of the color image data obtained by imaging the reference subject illuminated with the wide light (second light) with respect to the value of the component of the color image data obtained by imaging the reference subject illuminated with the white light WL (first light) is one tenth, the first light intensity ratio G1 is one tenth or a value obtained by multiplying one tenth by a constant (e.g., "a"), for example. The first ratio, which is obtained by imaging an imaging subject using the white light WL and the wide light is divided by the first light intensity ratio G1 for correction, and therefore the first ratio is multiplied by 10 or a value obtained by multiplying 10 by a constant (e.g., "1/a"), for example. Here, the component of the color image data may be the G component of the color image data including the wavelength band R0 as a wavelength band, but is preferably the luminance component, in light of the fact that the ratio of the light intensity level is accurately acquired. The reference subject need only be a subject determined such that it is used in common in multiple endoscope systems when performing examination for suppressing variation in a product between multiple endoscope systems, and for example, the reference subject may also be a reference white plate used for white balance, and may be biological tissue or a sample specified in advance. Here, the first corrected ratio Wide(Yh)/{WL(R)·G1} or Wide(Yh)/[{WL(R)+WL(G)}·G1] is the ratio between the luminance component and the R component or the total components of the R component and the G component, and therefore if the imaging sensitivity (value of the captured image data of the subject illuminated with light having the same light intensity) of the light receiving element of the imaging element 141 varies between the multiple endoscope systems, the first corrected ratio Wide(Yh)/{WL(R)·G1} or Wide(Yh)/[{WL(R)+WL(G)}·G1] also tends to vary between the multiple endoscope systems. For this reason, in the case of examining multiple endoscope systems, in order to make the imaging sensitivities of the image sensors uniform, it is preferable to use a reference image sensor for which the imaging sensitivity is guaranteed to be at a target sensitivity, which is used in common when performing examination of an endoscope system, instead of the image sensor 141. If the imaging sensitivity of the imaging sensor 141 matches the target sensitivity, the image sensor 141 can also be used.

Note that the first light intensity ratio G1 is a ratio that sets the ratio between the value of the luminance component of the color image data (first color image data) of the reference subject illuminated with the first light and the value of the luminance component of the color image data (second color image data) of the reference subject illuminated with the second light to a predetermined value, such as 1.0.

Figure 5:
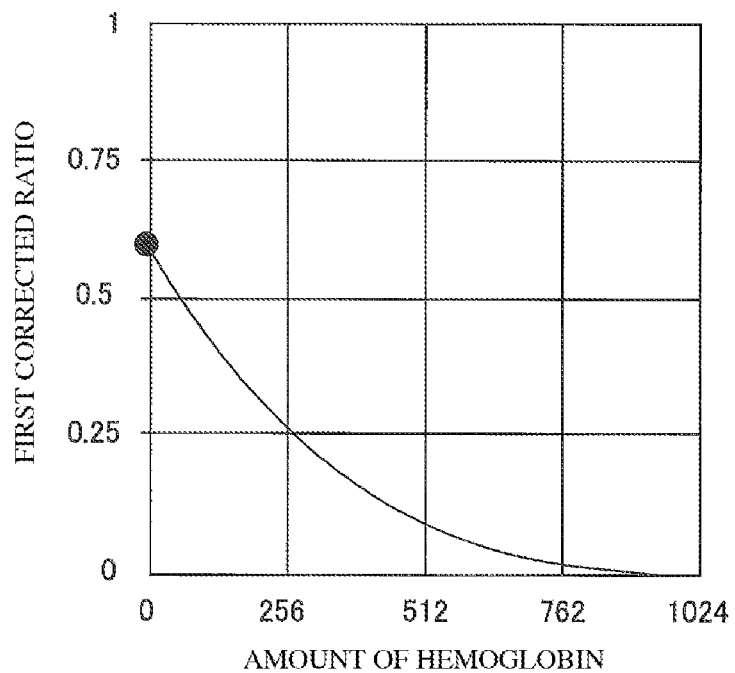
FIG. 5 is a diagram showing an example of a correlation between an amount of hemoglobin and a first corrected ratio, which are used in an embodiment.

Accordingly, even if the ratio between the light intensities of the first light and the second light vary between the endoscope systems, an amount of hemoglobin that does not vary between endoscope systems can be calculated using the correlation between the first corrected ratio and the amount of hemoglobin as shown in FIG. 5. As shown in FIG. 5, a reference table indicating the correlation between the first corrected ratio and the amount of hemoglobin is stored in the memory 512. FIG. 5 is a diagram showing an example of a correlation between an amount of hemoglobin and a first correction ratio, which are used in the present embodiment.

Correction of First Ratio: Imaging Sensitivity

In the above-described embodiment, the amount of hemoglobin in the biological tissue T is calculated based on the first ratio between the components of the color image data of the captured image generated by imaging the biological tissue T illuminated with the white light WL (first light) and the wide light (second light), which have different wavelength bands, with the image sensor 141, and therefore if the imaging sensitivity of the image sensor 141 varies between the multiple endoscope systems that perform examination, the amount of hemoglobin calculated based on the first ratio also tends to vary between the multiple endoscope systems. In this case, variation between the multiple endoscopes in the results of calculating the hemoglobin can be suppressed by separately correcting the reference tables used to calculate the hemoglobin for each endoscope system so as to match the variation of the imaging sensitivity of the image sensor 141, but it is complicated to re-create the reference table for each endoscope system. For this reason, the hemoglobin amount calculation unit 510a of the characteristic amount acquisition unit 510 corrects the ratio Wide(Yh)/WL(R) or Wide(Yh)/{WL(R)+WL(G)}, which is the first ratio. Specifically, the sensitivity ratio between the imaging sensitivity for the white light WL (first light) of the image sensor 141 and the imaging sensitivity for the wide light (second light) of the image sensor 141 is measured in advance, and the result is stored in the memory 512. When the amount of hemoglobin is to be calculated using the stored sensitivity ratio G2, the hemoglobin amount calculation unit 510a of the characteristic amount acquisition unit 510 calculates and acquires the amount of hemoglobin (first characteristic amount) of the biological tissue T using the reference table, based on the first corrected ratio Wide(Yh)/{WL(R)·G2} or Wide(Yh)/[{WL(R)+WL(G)}·G2], which is obtained by using the sensitivity ratio G2 to correct (divide) the ratio Wide(Yh)/WL(R) or Wide(Yh)/{WL(R)+WL(G)}, which is the first ratio. Accordingly, an amount of hemoglobin with little variation can be calculated even if the imaging sensitivity of the image sensor 141 varies between endoscope systems. Imaging sensitivity refers to the value of the color image data when light of the same light intensity is received at the same time by the image sensor 141. In the above-described embodiment, the first ratio is used to calculate the amount of hemoglobin, and therefore it is sufficient to use, as the imaging sensitivity, the sensitivity ratio between the imaging sensitivity for the white light WL (first light) and the imaging sensitivity for the wide light (second light) of the image sensor 141. Although the luminance component of the color image data and the R component and G component are used as the sensitivity ratio G2 in correspondence with the component of the color image data used for the first ratio, there is no particular limitation on the component to be used.

It is preferable that the above-described correction of the first ratio using this kind of sensitivity ratio G2 is performed under the condition that the intensity ratio of the light intensity of the white light WL (first light) and the wide light (second light) is at a target value. However, the intensity ratio of the light intensities varies between endoscope systems and is not constant in many cases, as described above. In this case, the hemoglobin amount calculation unit 510a of the characteristic amount acquisition unit 510 of the present embodiment preferably stores the above-described first light intensity ratio G1 in the memory 512 and uses the first light intensity ratio G1 and the sensitivity ratio G2 to calculate and acquire the amount of hemoglobin (first characteristic amount) of the biological tissue T using the reference table, based on the first corrected ratio Wide(Yh)/{WL(R)·G1·G2} or Wide(Yh)/[{WL(R)+WL(G)}·G1·G2] obtained by correcting (dividing) the ratio Wide(Yh)/WL(R) or Wide(Yh)/{WL(R)+WL(G)} using the first light intensity ratio G1 and the sensitivity ratio G2. Note that if the first light intensity ratio G1 is 1.0, the amount of hemoglobin (first characteristic amount) of the biological tissue T can be calculated and acquired using the reference table, based on the first corrected ratio Wide(Yh)/{WL(R)·G2} or Wide(Yh)/[{WL(R)+WL(G)}G2], using only the sensitivity ratio G2.

Note that the sensitivity ratio G2 is preferably a ratio obtained by using the first light intensity ratio G1 to correct a ratio between components of the color image data of the reference subject generated by imaging the reference subject illuminated with the white light WL (first light) and the wide light (second light) using the image sensor 141. For example, when the ratio between the R component WL(R) or the total components WL(R)+WL(G) of the R component and the G component of the color image data of a reference subject generated by imaging the reference subject, which has a hemoglobin amount of 0 and is illuminated with the white light WL (first light), using the image sensor 141, and the luminance component Wide(Yh) of the color image data of the reference subject generated by imaging the reference subject, which has a hemoglobin amount of 0 and is illuminated with wide light (second light), using the image sensor 141, is set to Wide(Yh)/WL(R) or Wide(Yh)/{WL(R)+WL(G)}, the sensitivity ratio G2 is set as Wide(Yh)/{WL(R)·G1·0.6} or Wide(Yh)/[{WL(R)+WL(G)}·G1·0.6]. Note that if the first light intensity ratio G1 is 1.0, the sensitivity ratio G2 can be set to Wide(Yh)/{WL(R)·0.6} or Wide(Yh)/[{WL(R)+WL(G)}·0.6]. Here, 0.6 is used in the equations above because the value of the first corrected ratio when the amount of hemoglobin is 0 is 0.6 as shown in FIG. 5. Accordingly, as shown in FIG. 5, even if the above-described imaging sensitivity varies between endoscope systems, the first corrected ratio when the amount of hemoglobin is 0 can be set to 0.6, and an amount of hemoglobin that does not vary between multiple endoscope systems can be calculated using a reference table used in common between the endoscope systems.

In this manner, the sensitivity ratio G2 is preferably a ratio set such that the value of the first corrected ratio obtained when a reference subject, e.g., a reference plate that does not have the same color component as the pigment of the hemoglobin, and for which the value of the first ratio is a known reference value, e.g., 0.6, is imaged with the image sensor 104 is the reference value of the reference subject, e.g., 0.6.

With the first ratio that is the correction target, the luminance component is used as the component of the second color image data, but it is also possible to use a G component that includes the wavelength region R0 as the wavelength region as the component of the second color image data.

The problem of the variation in the imaging sensitivity of the above-described image sensor 141 is not limited to the case of using two types of light with different wavelength bands as the illuminating light. For example, the problem of the variation occurs also in the case where the color image data is generated using light that includes light components with different wavelength bands and the amount of hemoglobin is calculated by obtaining a first ratio based on the corresponding components of the color image data corresponding to the wavelength bands of the above-described light components from the color image data.

According to an embodiment, the memory 512 stores, in advance, the sensitivity ratio, which is the ratio between the imaging sensitivities at different wavelength bands of the light components included in the light of the image sensor 141. At this time, the characteristic amount acquisition unit 510 preferably acquires the amount of hemoglobin based on the first corrected ratio obtained by using the sensitivity ratio to correct the first ratio, which is sensitive to the amount of hemoglobin, among the ratios of the corresponding components corresponding to the wavelength bands of the light components of the color image data.

Correction of Second Ratio: Light Intensity

In the above-described embodiment, the oxygen saturation Sat of the hemoglobin in the biological tissue T is calculated based on the amount of hemoglobin and the ratio Narrow(Yh)/Wide(Yh), which is the second ratio between the components of the color image data of the captured image of the biological tissue T illuminated with the wide light (second light) and the narrow light (third light), which have different wavelength bands, and therefore in order to calculate a reliable oxygen saturation Sat, it is preferable that the ratio between the light intensities of the above-described wide light (second light) and the narrow light (third light), which have different wavelength bands, is a predetermined value, or in other words, that the ratio between the light intensities is constant with no variation between multiple endoscope systems. However, the ratio between the light intensity of the wide light (second light) and the light intensity of the narrow light (third light) varies slightly due to manufacturing error or the like in each endoscope system in some cases. For this reason, the oxygen saturation Sat calculated based on the second ratio Narrow(Yh)/Wide(Yh) tends to vary between multiple endoscope systems. In this case, the variation in the result of calculating the oxygen saturation Sat between endoscope systems can be suppressed by correcting the lower limit value and the upper limit value of the second ratio used to calculate the oxygen saturation Sat to match the variation of the light intensity of the wide light (second light) and the light intensity of the narrow light (third light). However, it is complicated to re-create the above-described lower limit value and upper limit value in each endoscope system. For this reason, the oxygen saturation calculation unit 510b of the characteristic amount acquisition unit 510 of the present embodiment corrects the ratio Narrow(Yh)/Wide(Yh), which is the second ratio. Specifically, the second light intensity ratio G3, which is the ratio between the light intensity of the wide light (second light) and the light intensity of the narrow light (third light), is measured in advance, and the result of the measurement is stored in the memory 512. When the oxygen saturation Sat is calculated using the second ratio, the oxygen saturation calculation unit 510b of the characteristic amount acquisition unit 510 calculates and acquires the oxygen saturation Sat (second characteristic amount) of the hemoglobin in the biological tissue T using the upper limit value and the lower limit value based on the second corrected ratio Narrow(Yh)/{Wide(Yh)·G3} obtained by using the second light intensity ratio G3 to correct (divide) the ratio Narrow(Yh)/Wide(Yh), which is the second ratio. Note that the ratio Narrow(Yh)/Wide(Yh) is a parameter that is sensitive to the oxygen saturation Sat of the hemoglobin. Being sensitive means that when the oxygen saturation Sat of the hemoglobin changes, the ratio Narrow(Yh)/Wide(Yh) also changes according to the change.

As described above, the oxygen saturation Sat is calculated based on the second corrected ratio Narrow(Yh)/{Wide(Yh)·G3}, and therefore even if the ratio between the light intensity of the wide light (second light) and the light intensity of the narrow light (third light) varies between endoscope systems, the same oxygen saturation Sat can be calculated. With the light source apparatus 400 of the present embodiment, the wide light and the narrow light are transmission light that has passed through the optical filters 415 and 416 in the light irradiated from the one light source lamp 430, and therefore variation in the ratio between the light intensity of the wide light and the light intensity of the narrow light is caused by variation in the light transmittance of the optical filter 415 and the optical filter 416 or variation in the size (opening size) of the window 414a and the window 414b of the rotating filter 410.

The second light intensity ratio G3 stored in the memory 512 is preferably the ratio between components of the color image data of a reference subject generated by imaging the reference subject illuminated with the wide light (second light) and the narrow light (third light) using the image sensor 141 or a reference image sensor. More specifically, the second light intensity ratio G3 is a value obtained by dividing the value of a component of the color image data of the reference subject generated by imaging the reference subject illuminated with the narrow light (third light) using the image sensor 141 or a reference image sensor, by the value of a component of the color image data of the reference subject generated by imaging the reference subject illuminated with the white light WL (first light) with the image sensor 141 or the reference image sensor, or a value obtained by multiplying this value by a constant.

Thus, according to an embodiment, the second light intensity ratio G3 is a coefficient that corrects the second ratio such that even if the light intensities of the wide light (second light) and the narrow light (third light) vary, the value of the second ratio is the value of the second ratio obtained from a component of the color image data corresponding to the wide light and the narrow light of the light intensity determined in advance. For example, if the value of the component of the color image data obtained by imaging the reference subject illuminated with the narrow light (third light) with respect to the value of the component of the color image data obtained by imaging the reference subject illuminated with the wide light (second light) is one tenth, the second light intensity ratio G3 is one tenth or a value obtained by multiplying one tenth by a constant (e.g., "a"), for example. The second ratio, which is obtained by imaging the imaging subject using this kind of wide light and narrow light, is divided by the second light intensity ratio G3 for correction, and therefore a value obtained by multiplying by 10 or by multiplying a constant (e.g., "1/a") by 10, for example, is multiplied by the second ratio. Here, the component of the color image data may be the G component of the color image data including the wavelength band R0 as a wavelength band, but is preferably the luminance component in light of the fact that the ratio of the light intensity level is accurately acquired. The reference subject need only be an imaging subject determined such that it is used in common in multiple endoscope systems when performing examination for suppressing variation in a product between multiple endoscope systems, and for example, the reference subject may also be a reference white plate used for white balance, and may be biological tissue or a sample specified in advance.

Figure 6:
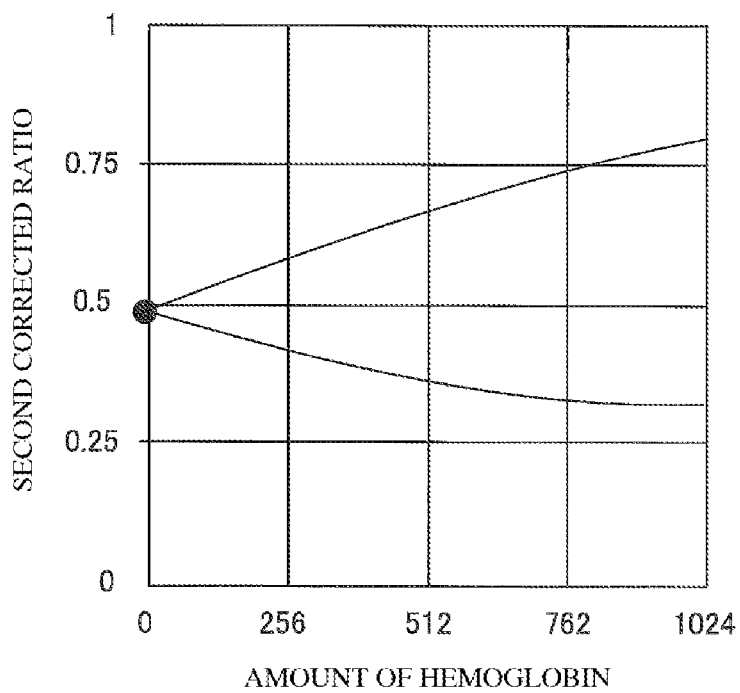
FIG. 6 is a diagram showing an example of a correlation between an oxygen saturation Sat of hemoglobin and a second corrected ratio, which are used in an embodiment.

Specifically, the second light intensity ratio G3 is preferably determined such that the ratio between the luminance components of the color image data of the reference subject, which has an oxygen saturation Sat of 0% and is illuminated with the wide light (second light) and the narrow light (third light) is 0.49 (in FIG. 6, the oxygen saturation Sat is 0% at a second corrected ratio of 0.49. Specifically, when the ratio between the luminance component of the color image data of the above-described reference subject illuminated with the wide light (second light) and the narrow light (third light) is set to Narrow(Yh)/Wide(Yh), the second light intensity ratio G3 is determined to be Narrow(Yh)/{Wide(Yh)·0.49}. Accordingly, as shown in FIG. 6, even if the ratio between the light intensity of the wide light (second light) and the light intensity of the narrow light (third light) varies between endoscope systems, the second corrected ratio for when the oxygen saturation Sat is 0% can be uniformly set to 0.49, and the oxygen saturation Sat of the hemoglobin with no variation between endoscope systems can be calculated. FIG. 6 is a diagram showing an example of a correlation between an oxygen saturation Sat of hemoglobin and a second correction ratio, which are used in an embodiment.

Also, the second corrected ratio Narrow(Yh)/{Wide(Yh)·G3} is the ratio between two luminance components, and therefore if the imaging sensitivity of the light receiving elements of the image sensor 141 (the value of the captured image data of the imaging subject illuminated with the same light intensity) varies between multiple endoscope systems, the second corrected ratio Narrow(Yh)/{Wide(Yh)·G3} also tends to vary between multiple endoscope systems. For this reason, in the case of examining multiple endoscope systems, in order to unify the imaging sensitivities of the image sensors, it is preferable to use a reference image sensor for which the imaging sensitivity is guaranteed to be a target sensitivity, which is used in common when performing examination of an endoscope system, instead of the image sensor 141. If the imaging sensitivity of the imaging sensor 141 matches the target sensitivity, the image sensor 141 can also be used.

The oxygen saturation calculation unit 510b of the characteristic amount acquisition unit 510 calculates the oxygen saturation Sat of the hemoglobin based on the amount of hemoglobin and the second corrected ratio obtained by correcting the second ratio using the second light intensity ratio G3, but when the amount of hemoglobin to be used at this time is calculated, it is preferable that the amount of hemoglobin is calculated based on the first corrected ratio corrected using the first light intensity ratio G1, based on the first corrected ratio corrected using the sensitivity ratio G2, or based on the first corrected ratio corrected using the first light intensity ratio and the sensitivity ratio G2.

Characteristic Amount Calculation Method 1

In this kind of endoscope system 1, calculation of the characteristic amounts is performed as follows.

The biological tissue T is illuminated with the white light WL (first light) and the wide light (second light), which have different wavelength bands and are emitted through the insertion tube 110 of the electronic endoscope 100 from the light source apparatus 430.

At this time, the first color image data is generated by imaging the biological tissue T illuminated with the white light WL (first light) using the image sensor 141, and the second color image data is generated by imaging the biological tissue T illuminated with the wide light (second light) using the image sensor 141.

The hemoglobin amount calculation unit 510a of the characteristic amount acquisition unit 510 of the processor 200 generates a first corrected ratio, such as Wide(Yh)/{WL(R)·G1} or Wide(Yh)/[{WL(R)+WL(G)}·G1], which is obtained by using a pre-acquired first light intensity ratio G1, which is the ratio between the light intensity of the white light WL (first light) and the light intensity of the wide light (second light), to correct the first ratio, such as Wide(Yh)/WL(R) or Wide(Yh)/{WL(R)+WL(G)}, which is sensitive to the amount of hemoglobin (first characteristic amount) of the biological tissue T, among the ratios between the multiple components of the first color image data of the biological tissue T and the multiple components of the second color image data of the biological tissue T.

Furthermore, the hemoglobin amount calculation unit 510a of the characteristic amount acquisition unit 510 calculates the amount of hemoglobin (first characteristic amount) of the biological tissue T based on the generated first corrected ratio using a reference table indicating a relationship such as that shown in FIG. 5, for example.

Characteristic Amount Calculation Method 2

Also, in the endoscope system 1, calculation of the characteristic amounts, which is different from the characteristic amount calculation method 1, is performed as follows.

The biological tissue T is illuminated with the white light WL (first light) and the wide light (second light), which have different wavelength bands and are emitted through the insertion tube 110 of the electronic endoscope 100 from the light source apparatus 430.

At this time, the first color image data is generated by imaging the biological tissue T illuminated with the white light WL (first light) using the image sensor 141, and the second color image data is generated by imaging the biological tissue T illuminated with the wide light (second light) using the image sensor 141.

The hemoglobin amount calculation unit 510a of the characteristic amount acquisition unit 510 of the processor 200 generates a first corrected ratio, such as Wide(Yh)/{WL(R)·G2} or Wide(Yh)/[{WL(R)+WL(G)}·G2], which is obtained by using a pre-acquired sensitivity ratio G2, which is the ratio between the imaging sensitivity for the white light WL (first light) and the imaging sensitivity for the wide light (second light) of the image sensor 141, to correct the first ratio, such as the ratio Wide(Yh)/WL(R) or Wide(Yh)/{WL(R)+WL(G)}, which is sensitive to the amount of hemoglobin (first characteristic amount) of the biological tissue T, among the ratios between the multiple components of the second color image data of the biological tissue T and the multiple components of the first color image data of the biological tissue T.

Furthermore, the hemoglobin amount calculation unit 510a of the characteristic amount acquisition unit 510 calculates the amount of hemoglobin (first characteristic amount) of the biological tissue T based on the generated first corrected ratio using a reference table indicating a relationship such as that shown in FIG. 5, for example.

Characteristic Amount Calculation Method 3

Furthermore, in the endoscope system 1, calculation of the characteristic amounts, which is different from the characteristic amount calculation methods 1 and 2, is performed as follows.

The biological tissue T is illuminated with the white light WL (first light), the wide light (second light), and the narrow light (third light), which have different wavelength bands and are emitted through the insertion tube 110 of the electronic endoscope 100 from the light source apparatus 430.

Next, the second color image data is generated by imaging the biological tissue T illuminated with the wide light (second light) using the image sensor 141, and the third color image data is generated by imaging the biological tissue T illuminated with the narrow light (third light).

The oxygen saturation calculation unit 510b of the characteristic amount acquisition unit 510 of the processor 200 generates the second corrected ratio, e.g., Narrow(Yh)/{Wide(Yh)·G3}, which is obtained by using the pre-acquired second light intensity ratio G3, which is the ratio between the light intensity of the wide light (second light) and the light intensity of the narrow light (third light), to correct the second ratio, e.g., Narrow(Yh)/Wide(Yh), which is sensitive to the oxygen saturation Sat (second characteristic amount) of the hemoglobin in the biological tissue T, among the ratios between the multiple components of the second color image data of the biological tissue T and the multiple components of the third color image data of the biological tissue T.

Furthermore, the oxygen saturation calculation unit 510b of the characteristic amount acquisition unit 510 calculates the oxygen saturation Sat (second characteristic amount) of the hemoglobin in the biological tissue T based on the second corrected ratio.

At this time, the white light WL (first light), along with the wide light (second light), is used to obtain the above-described first ratio, e.g., Wide(Yh)/WL(R) or Wide(Yh)/{WL(R)+WL(G)}, which is sensitive to the amount of hemoglobin, using the hemoglobin amount calculation unit 510a. The first ratio is used to obtain the amount of hemoglobin using the characteristic amount calculation methods 1 and 2. The oxygen saturation calculation unit 510b uses the amount of hemoglobin to calculate the oxygen saturation Sat of the hemoglobin.

In addition to the above-described characteristic amount calculation methods 1 to 3, the following calculation of the characteristic amount can also be performed as an embodiment.

That is, the light source apparatus 400 illuminates biological tissue with light having at least two light components with different wavelength bands. By imaging the illuminated biological tissue using the image sensor 104, the image processing unit 500 generates color image data. At this time, the characteristic amount acquisition unit 510, or more specifically, the hemoglobin amount calculation unit 510a, generates the first corrected ratio, which is obtained by using the pre-acquired sensitivity ratio G3, which is the ratio of imaging sensitivities between wavelength bands of different light components of the image sensor 104, to correct the first ratio that is sensitive to the amount of hemoglobin in the biological tissue, among the ratios of the corresponding components corresponding to the wavelength bands of the light components of the color image data of the biological tissue. The hemoglobin amount calculation unit 510a calculates the amount of hemoglobin in the biological tissue based on the generated first corrected ratio.

Operation of Endoscope System

The endoscope system 1 has two operation modes, namely a normal observation mode and an analysis mode. The normal observation mode is an operation mode in which a color image is captured using white light WL generated by the optical filter 418. The analysis mode is a mode in which analysis is performed based on digital image data obtained by performing imaging using the wide light, the narrow light, and the white light WL, which have passed through the optical filters 415, 416, and 418, and a distribution image (e.g., an oxygen saturation distribution image) of biological information of the biological tissue T is displayed. The operation mode of the endoscope system 1 is switched through a user operation performed on an operation panel (not shown) of the processor 200 or an operation button (not shown) of the electronic endoscope 100, for example.

In the normal observation mode, the controller 516 controls a moving mechanism in the light source apparatus 400 to move the rotating filter 410 from an applied position to a retracted position. Note that in the analysis mode, the rotating filter 410 is arranged at the applied position. Also, if the rotating filter 410 does not include a moving mechanism, the controller 516 is configured to stop the rotating filter 410 at the position at which the light irradiated from the light source lamp 430 is incident on the optical filter 418 by controlling the filter control unit 420. Then, after predetermined image processing such as demosaicing is implemented on the digital image data generated by imaging performed by the imaging element 141, the result is converted into a video signal and is subjected to screen display on the display 300.

In the analysis mode, the controller 516 controls the filter control unit 420 and sequentially performs imaging of the biological tissue T using the light that has passed through the optical filters 415, 416, and 418 while driving the rotating filter 410 so as to rotate at a certain rotation rate. Also, the controller 516 generates an image showing a distribution of biological information in the biological tissue T, based on the digital image data acquired using the wide light and the narrow light generated by the optical filters 415 and 416 respectively. The image display control unit 514 generates a display image in which an image indicating the distribution of the biological information is aligned with or overlaid on the normal observation image acquired using the optical filter 418. The post-image processing unit 508 further converts the data of the generated display image into a video signal and sends it to the display 300 so that the display 300 subjects it to screen display.

In the analysis mode, the timings of the optical filters 515, 516, and 518, which cross the optical path of the light from the light source lamp 430, or in other words, the phase of the rotation of the rotating filter 410, is compared with the phase of a timing signal that is synchronized with the driving of the image sensor 141 and is supplied from the controller 516 by the filter control unit 420, and is adjusted.

Figure 7:
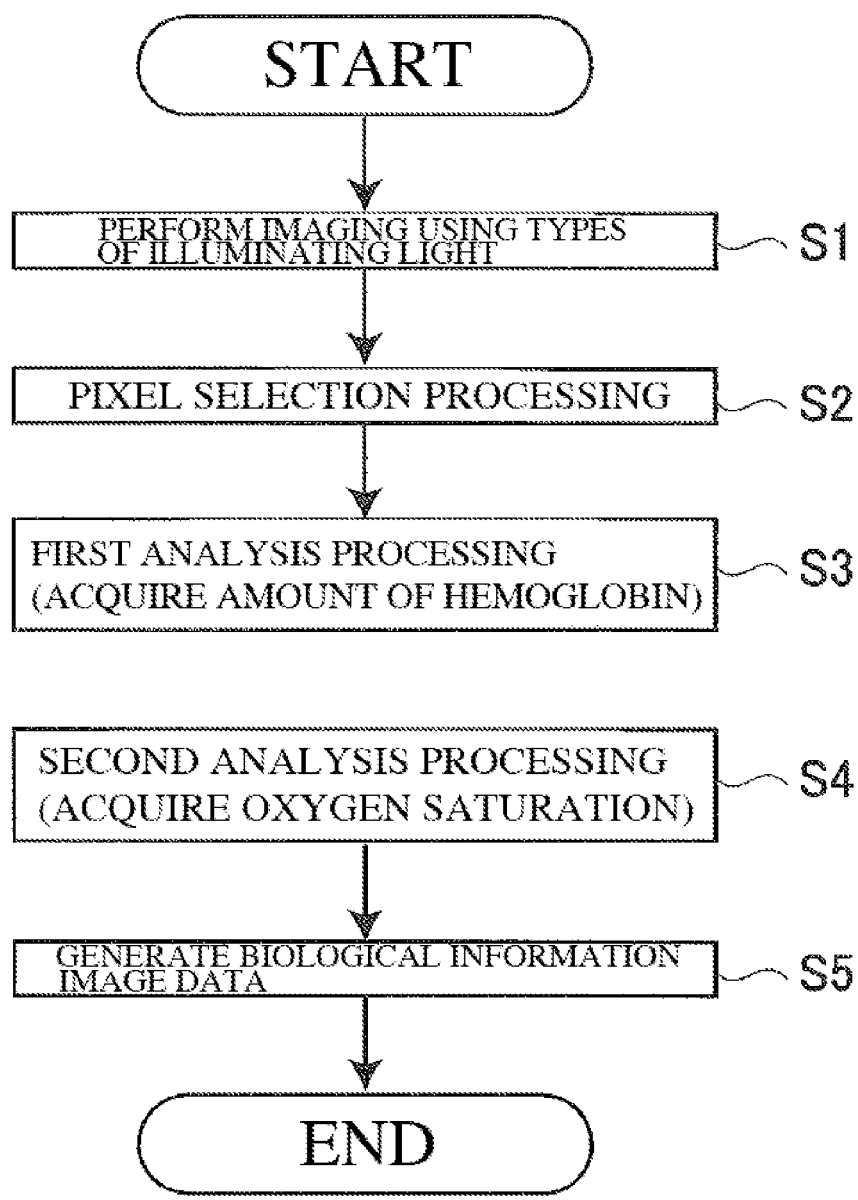
FIG. 7 is a flowchart illustrating an example of processing in an endoscope system of an embodiment.

Next, analysis processing executed in the analysis mode will be described. FIG. 7 is a flowchart showing a procedure of analysis processing.

If the analysis mode is selected through a user operation, as described above, the filter control unit 420 drives the rotating filter 410 so as to rotate at a certain rotation rate. Also, the types of illuminating light IL (wide light, narrow light, and white light WL) that have passed through the optical filters 415, 416, and 418 are sequentially supplied to the light source apparatus 400 and imaging using the each type of illuminating light IL is sequentially performed (step S1). Specifically, data on the R component, the G component, and the B component of the second, third, and first color image data of the biological tissue T that was imaged using the wide light, the narrow light, and the white light WL that have passed through the optical filters 415, 416, and 418 and have been subjected to pre-image processing is stored in the memory 512. The white light WL is not strictly limited to white light including all frequency components of visible light. The white light WL need only include light of specific wavelength bands, such as R (red), G (green), and B (blue), which are reference colors, for example. That is, the white light WL also includes light that includes wavelength components from green light to red light, light that includes wavelength components from blue light to green light, and the like, for example.

Next, the characteristic amount acquisition unit 510 calls the first color image data of the white light WL from the memory 512 and performs pixel selection processing S2 for selecting the pixels to be subjected to the analysis processing below (processes S3 to S8) from the pixels of the first color image data. Even if the oxygen saturation and the blood flow amount are calculated based on the color information of the pixels, significant values are not obtained for locations that do not include blood in the biological tissue and locations in which the color of the biological tissue receives an overriding influence from a substance other than hemoglobin, and these locations merely result in noise. If this kind of noise is provided to the operator, it not only hinders the judgment performed by the operator, but also reduces the processing speed due to applying a needless load to the characteristic amount acquisition unit 510. In view of this, in the analysis processing shown in FIG. 7, a configuration is used in which pixels that are suitable for analysis processing, or in other words, pixels in which spectral characteristics of hemoglobin are stored, are selected, and the analysis processing is performed only on the selected pixels.

Specifically, in the pixel selection processing S2, only the pixels that satisfy all of the following three conditional equations are selected as the target pixels for the analysis processing.

Equation (4):

$$B(x,y)/G(x,y) > a_1 \quad \text{Equation 4}$$

Equation (5):

$$R(x,y)/G(x,y) > a_2 \quad \text{Equation 5}$$

Equation (6):

$$R(x,y)/B(x,y) > a_3 \quad \text{Equation 6}$$

Here, $a_1$, $a_2$, and $a_3$ are positive constants.

The above-described three conditional equations are set based on the magnitude relationship of the values, namely, G component<B component<R component, in the transmission spectrum of the blood. Note that the pixel selection processing S2 may also be performed using only one or two of the above-described three conditional equations (e.g., using only Equation 5 and Equation 6, with attention given to the red color unique to blood).

Next, the hemoglobin amount calculation unit 510a of the characteristic amount acquisition unit 510 calls the first color image data and the second color image data from the memory 512 and performs the first analysis processing (S3) on the selected pixels. Specifically, the hemoglobin amount calculation unit 510a obtains the R component WL(R) of the first color image data or the total components WL(R)+WL(G) of the R component and the G component, and further obtains the luminance component Wide(Yh) of the second color image data and obtains the first ratio. Furthermore, the hemoglobin amount calculation unit 510a calculates a first corrected ratio using at least one of the first light intensity ratio G1 and the sensitivity ratio G2 stored in the memory 512, and calculates and obtains the amount of hemoglobin in the biological tissue T by referencing the reference table stored in the memory 512, based on the first corrected ratio.

Next, the oxygen saturation calculation unit 510b of the characteristic amount acquisition unit 510 performs the second analysis processing S4 on the selected pixels. Specifically, the oxygen saturation calculation unit 510b obtains the luminance component Wide(Yh) of the second color image data and further obtains the luminance component Narrow(Yh) of the third color image data and obtains the second ratio. Furthermore, the oxygen saturation calculation unit 510b calculates the second corrected ratio using the second light intensity ratio G3 stored in the memory 512, calls the upper limit value and the lower limit value stored in the memory 512 based on the second corrected ratio, and calculates and obtains the oxygen saturation Sat of the hemoglobin in the biological tissue T.

The data of the distribution image of the calculated oxygen saturation Sat and the distribution image of the amount of hemoglobin are sent along with the first color image data to the image display control unit 514.

The image display control unit 514 receives an input instruction from the operator via the controller 516 and generates the biological information image data (S5). Furthermore, the post-image processing unit 508 generates screen data for displaying a display by performing signal processing (γ correction, etc.) on the biological information screen data. The generated screen data is sent to the display 300, and the display 300 displays the biological information image. In response to the input instruction of the operator, the image display control unit 514 can generate various types of screen data, such as a display screen for displaying only a distribution image of the amount of hemoglobin or an oxygen saturation distribution image, a display screen displaying only a normal observation image, or a display screen displaying supplementary information such as ID information of the patient, observation conditions, and the like overlaid on a distribution image of the amount of hemoglobin, the oxygen saturation distribution image, and/or the normal observation image.

Figure 8:
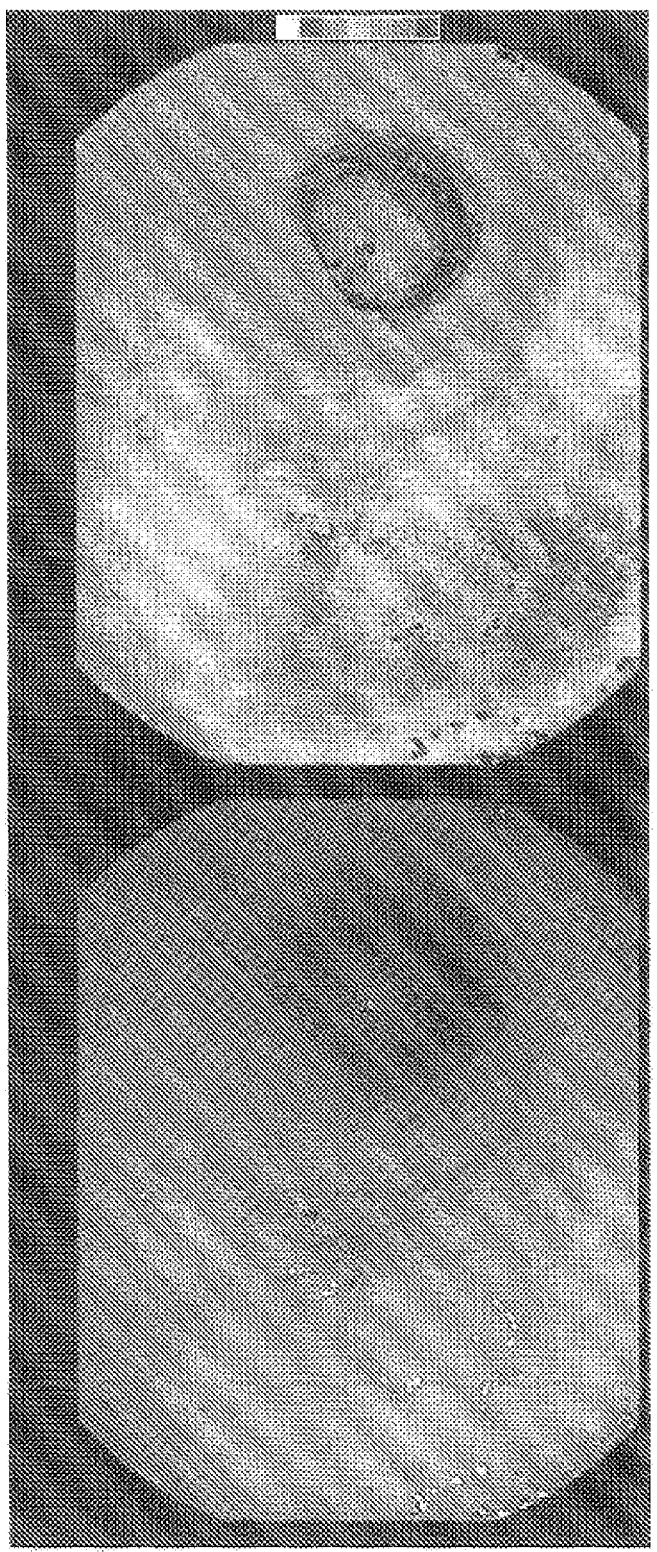
FIG. 8 is a diagram showing an example of an image displayed by a display of an endoscope system of an embodiment.

FIG. 8 is a diagram showing an example of an image displayed by the display 300. FIG. 8 is an example of a display of the oxygen saturation distribution image (two-dimensional display) generated from the oxygen saturation Sat acquired through the above-described processing. The normal observation image (left side in FIG. 8) obtained when the white light WL is used as the illuminating light and the oxygen saturation distribution image (right side in FIG. 8) are displayed in parallel. The oxygen saturation distribution image is subjected to gradation display, in which the hue changes according to the oxygen saturation. Parts with high and low oxygen saturations can be specified using the oxygen saturation distribution image.

It is known that in a lessened part of a malignant tumor, the amount of hemoglobin is greater than that of normal biological tissue due to angiogenesis, and the oxygen saturation Sat is lower than that of normal biological tissue since oxygen metabolism is prominent. For this reason, it is important to display the distribution image of the amount of hemoglobin and the oxygen saturation distribution image. The image display control unit 514 may also implement emphasis display processing on the pixels that satisfy predetermined conditions of the distribution images and display the result.

In the present embodiment, in order to perform highly-accurate diagnosis using the endoscope system 1, it is required that the oxygen saturation distribution image indicating the distribution of the oxygen saturation Sat has high image quality. For this reason, the oxygen saturation distribution image preferably has 1 million pixels or more, more preferably 2 million pixels or more, and even more preferably 8 million pixels or more. On the other hand, the greater the number of pixels in the image being handled is, the larger the arithmetic circuit of the processor 200 tends to be, and the greater the processing load also tends to be. In particular, with a high number of pixels (high image quality) of 1 million pixels or more, the above-described tendency is prominent. In the present embodiment, as described above, a reference table in which the amount of hemoglobin, the oxygen saturation Sat, and the color image data is associated, and information on the correlation are provided in advance, and the amount of hemoglobin and the oxygen saturation Sat are calculated using the reference table and the correlation, and therefore in the above-described embodiment, the amount of hemoglobin and the oxygen saturation Sat can be calculated efficiently compared to the case of calculating the amount of hemoglobin and the oxygen saturation each time the color image data is acquired and without using the reference table and the correlation. For this reason, the arithmetic circuit of the processor 200 can be made smaller, and thus a processor 200 with a low cost, low heat generation, and low power consumption can be provided even if an image with high image quality is to be generated.

In the above description, an embodiment has been described, but the present disclosure is not limited to the above-described configuration, and various modifications are possible within the range of the technical idea of the present disclosure.

REFERENCE SIGNS LIST

1 Endoscope system
100 Electronic endoscope
110 Insertion tube
111 Insertion tube leading end portion
121 Object lens group
131 Light guide
131*a* Leading end portion
131*b* Base end portion
132 Lens
141 Image sensor
141*a* Color filter
142 Cable
200 Processor
300 Display
400 Light source apparatus
410 Rotating filter
420 Filter control unit
430 Light source lamp
440 Light condensing lens
450 Light condensing lens
500 Image processing unit
502 A/D conversion circuit
504 Pre-image processing unit
506 Frame memory unit
508 Post-image processing unit
510 Characteristic amount acquisition unit
512 Memory
514 Image display control unit
516 Controller

The invention claimed is:

1. An endoscope system, comprising:
a light source apparatus configured to emit at least first light and second light with different wavelength bands;
an endoscope including an imaging unit that includes an image sensor configured to generate first color image data by imaging biological tissue illuminated with the first light, and to generate second color image data by imaging the biological tissue illuminated with the second light; and
a processor including: a storage unit storing a first light intensity ratio, which is a ratio between a light intensity of the first light and a light intensity of the second light; and a characteristic amount acquisition unit configured to acquire a first characteristic amount of the biological tissue based on a first corrected ratio obtained by using the first light intensity ratio to correct a first ratio that is sensitive to the first characteristic amount of the biological tissue, among ratios between a plurality of components of the first color image data of the biological tissue and a plurality of components of the second color image data.

2. The endoscope system according to claim 1, wherein the first light intensity ratio is a ratio between components of color image data of a reference subject, the color image data being generated by imaging the reference subject illuminated with the first light and the second light using the image sensor or a reference image sensor.

3. The endoscope system according to claim 1, wherein the first light intensity ratio is a ratio for setting a ratio between a value of a luminance component of the first color image data and a value of a luminance component of the second color image data of the reference subject to a certain value.

4. The endoscope system according to claim 1, wherein
the first characteristic amount is an amount of hemoglobin in the biological tissue, and
the first ratio is a ratio between a luminance component of the second color image data and an R component of the first color image data or between a luminance component of the second color image data and the total components of the R component and a G component of the first color image data.

5. The endoscope system according to claim 1, wherein in the wavelength band of the second light, one component of the second color image data includes a wavelength band that is sensitive to change in an amount of hemoglobin in the biological tissue but is not sensitive to change in an oxygen saturation of the hemoglobin.

6. An endoscope system, comprising:
a light source apparatus configured to emit first light, second light, and third light with different wavelength bands;
an endoscope including an imaging unit that includes an image sensor configured to generate second color image data by imaging biological tissue illuminated with the second light, and to generate third color image data by imaging the biological tissue illuminated with the third light; and
a processor including: a storage unit storing a second light intensity ratio, which is a ratio between a light intensity of the second light and a light intensity of the third light; and a characteristic amount acquisition unit configured to acquire a second characteristic amount of the biological tissue based on a second corrected ratio obtained by using the second light intensity ratio to correct a second ratio that is sensitive to the second characteristic amount of the biological tissue, among ratios between a plurality of components of the second color image data of the biological tissue and a plurality of components of the third color image data of the biological tissue.

7. The endoscope system according to claim 6, wherein the second light intensity ratio is a ratio between components of color image data of a reference subject, the color image data being generated by imaging the reference subject illuminated with the second light and the third light using the image sensor or a reference image sensor.

8. The endoscope system according to claim 6, wherein
the imaging unit is configured to generate first color image data by imaging biological tissue illuminated with the first light, using the image sensor;
the storage unit stores a first light intensity ratio, which is a ratio between a light intensity of the first light and the light intensity of the second light; and the characteristic amount acquisition unit includes a first portion configured to acquire a first characteristic amount of the biological tissue based on a first corrected ratio obtained by using the first light intensity ratio to correct a first ratio that is sensitive to the first characteristic amount of the biological tissue, among ratios of a plurality of components of the first color image data of the biological tissue and a plurality of components of the second color image data of the biological tissue, and a second portion configured to acquire the second characteristic amount of the biological tissue based on the first characteristic amount and the second corrected ratio.

9. The endoscope system according to claim 6, wherein
the imaging unit generates first color image data by imaging biological tissue illuminated with the first light, using the image sensor,
the storage unit stores a sensitivity ratio, which is a ratio between an imaging sensitivity for the first light and an imaging sensitivity for the second light of the image sensor, and
the characteristic amount acquisition unit includes a first portion configured to acquire a first characteristic amount of the biological tissue based on a first corrected ratio obtained by using the sensitivity ratio to correct a first ratio that is sensitive to the first characteristic amount of the biological tissue, among ratios of a plurality of components of the first color image data of the biological tissue and a plurality of components of the second color image data of the biological tissue, and a second portion configured to acquire the second characteristic amount of the biological tissue based on the first characteristic amount and the second corrected ratio.

10. The endoscope system according to claim 9, wherein the sensitivity ratio is a ratio set such that a value of the first corrected ratio obtained when a reference subject, for which a value of the first ratio is a known reference value, is imaged using the image sensor is the known reference value.

11. The endoscope system according to claim 6, wherein
the imaging unit generates first color image data by imaging biological tissue illuminated with the first light, using the image sensor,
the storage unit stores a first light intensity ratio, which is a ratio between a light intensity of the first light and the light intensity of the second light, and a sensitivity ratio, which is a ratio between an imaging sensitivity for the first light and an imaging sensitivity for the second light of the image sensor, and
the characteristic amount acquisition unit includes a first portion configured to acquire a first characteristic amount of the biological tissue based on a first corrected ratio obtained by using the sensitivity ratio and the first light intensity ratio to correct a first ratio that is sensitive to the first characteristic amount of the biological tissue, among ratios of a plurality of components of the first color image data of the biological tissue and a plurality of components of the second color image data of the biological tissue, and a second portion configured to acquire the second characteristic amount of the biological tissue based on the first characteristic amount and the second corrected ratio.

12. The endoscope system according to claim 6, wherein
the second characteristic amount is an oxygen saturation of hemoglobin in the biological tissue, and
the second ratio is a ratio between a luminance component of the third color image data and a luminance component of the second color image data.

13. The endoscope system according to claim 6, wherein the wavelength band of the third light is included in the wavelength band of the second light.

14. The endoscope system according to claim 6, wherein in the wavelength band of the third light, one component of the third color image data includes a wavelength band that is sensitive to change in an oxygen saturation of the biological tissue.

15. The endoscope system according to claim 6, wherein the light source apparatus has a configuration for emitting light with different wavelength bands by sequentially switching a plurality of optical filters on an optical path.

16. The endoscope system according to claim 15, wherein the second light is filtered light of the first light obtained by using one of the optical filters to transmit a first wavelength band within a range of 500 nm to 600 nm in the wavelength band of the first light, and the third light is filtered light of the first light obtained by using one of the optical filters to transmit a second wavelength band that is narrower than the first wavelength band and is within the range of the first wavelength band.

17. A biological tissue characteristic amount calculation method, comprising:
a step of illuminating biological tissue with first light, second light, and third light with different wavelength bands;
a step of generating second color image data by imaging the biological tissue illuminated with the second light using an image sensor, and generating third color image data by imaging the biological tissue illuminated with the third light;
a step of generating a second corrected ratio obtained by using a pre-acquired second light intensity ratio, which is a ratio between a light intensity of the second light and a light intensity of the third light, to correct a second ratio that is sensitive to a second characteristic amount of the biological tissue, among ratios between a plurality of components of the second color image data of the biological tissue and a plurality of components of the third color image data of the biological tissue; and
a step of calculating the second characteristic amount of the biological tissue based on the second corrected ratio.

* * * * *